United States Patent [19]

Parsons et al.

[11] Patent Number: 5,145,990
[45] Date of Patent: * Sep. 8, 1992

[54] PHOSPHOROUS CONTAINING DHP ENZYME INHIBITORS

[75] Inventors: William H. Parsons, Rahway; William R. Schoen, Edison; Arthur A. Patchett, Westfield, all of N.J.

[73] Assignee: Merck & Co., Inc., Rahway, N.J.

[*] Notice: The portion of the term of this patent subsequent to Dec. 29, 2004 has been disclaimed.

[21] Appl. No.: 642,692

[22] Filed: Jan. 9, 1991

Related U.S. Application Data

[63] Continuation of Ser. No. 264,241, Oct. 28, 1988, abandoned.

[51] Int. Cl.$^5$ .................... C07F 9/30; A61K 31/13; A61K 31/185; A61K 31/66
[52] U.S. Cl. .................... 562/16; 514/79; 514/80; 514/82; 514/89; 514/94; 514/95; 514/96; 514/99; 514/100; 514/114; 546/22; 546/23; 548/112; 548/113; 549/5; 549/6; 549/218; 549/220
[58] Field of Search .................... 562/16; 514/79, 80, 514/82, 89, 94, 95, 96, 99, 100, 114; 546/22, 23; 548/5, 6; 549/5, 6, 218, 220

[56] References Cited

U.S. PATENT DOCUMENTS

| | | | |
|---|---|---|---|
| 4,147,780 | 4/1979 | Dingwall et al. | 424/211 |
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |
| 4,374,131 | 2/1983 | Petrillo, Jr. | 514/91 |
| 4,416,833 | 11/1983 | Karanewsky et al. | 260/941 |
| 4,539,208 | 9/1985 | Kahen et al. | 514/195 |
| 4,715,994 | 12/1987 | Parsons et al. | 514/89 |

FOREIGN PATENT DOCUMENTS

| | | |
|---|---|---|
| 0091594 | 10/1983 | European Pat. Off. |
| 161546 | 11/1985 | European Pat. Off. |
| 209848 | 1/1987 | European Pat. Off. |
| 210545 | 2/1987 | European Pat. Off. |

OTHER PUBLICATIONS

F. Arndt, Organic Syn. Coll. V II 165–167, p. 33 (1943).
F. R. Atherton et al., Antimicrobial Agents & Chemoth. 15, 677 (1979).
P. A. Bartlett and W. B. Kezer, J. Amer. Chem. Soc. 106 4282–4283 (1979).
E. K. Baylis et al., J. Chem. Soc. Perkin Trans 1 2845–2853 (1984).
M. Bergmann & H. Schleich, Z. Physiol. Chem. Soc 205, pp. 65–75 (1966).
B. J. Campbell et al., Biochem. Biophys. Acta 118, pp. 371–386 (1966).
Chem Abstracts, vol. 107, No. 11, No. 97134K (1987).
Chem Abstracts, vol. 107 (9) No. 78250d (1987).
Chaiet et al., J. Antibiotics 37 (3) 207–210 (1984).
Gundermann et al., Chem. Bes. 94 3254 (1961).
F. M. Kahan et al., J. Antimicrobial Chemo. 12, Suppl. D. 1–35 (1983).
Lesiak et al., Polish J. Chem. 53 327 (1979).
Neuhaus, J. Biol. Chem., 778 (1962).
F. C. Neuhaus & W. P. Hammes, Pharm. Ther. 14 265–319 (1981).
F. C. Neuhaus & J. L. Lynch, Biochemistry 3 471–480 (1964).
F. C. Neuhaus et al., Biochemistry 8 5119–5124 (1969).
A. Rahman et al., Tetrahedron 36, 1063–1070 (1980).
E. D. Thorsett et al. (Merck & Co., Inc., Proc. Natl. Acad. Sci., U.S.A., vol. 79, 2176–2180 (Apr. 1982).
J. K. Thottathil et al., Tetrahedron Lett. 25, 4737–4740, 4741–4744 (1984).

*Primary Examiner*—Joseph E. Evans
*Attorney, Agent, or Firm*—Frank P. Grassler; Joseph F. DiPrima

[57] ABSTRACT

Compounds of the formula:

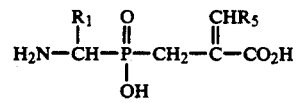

wherein $R_1$ is $C_2$-$C_{12}$ linear or branched unsubstituted alkyl; $C_1$-$C_{12}$ linear or branched substituted alkyl; $C_2$-$C_{12}$ linear or branched monoalkenyl; $C_2$-$C_{12}$ linear or branched alkynyl; $C_7$-$C_{20}$ aralkyl, wherein the alkyl chain is linear or branched $C_1$-$C_8$ and the aryl moiety is $C_6$-$C_{12}$; $C_4$-$C_{10}$ cycloalkylalkyl; $C_3$-$C_7$ cycloalkyl; wherein these values for $R_1$, other than $C_2$-$C_{12}$ linear or branched unsubstituted alkyl, can be substituted by one or more of $C_1$-$C_4$ alkoxy, $C_3$-$C_6$ cycloalkyloxy, $C_3$-$C_6$ cycloalkylthio, $C_6$-$C_{12}$ aryloxy, $C_1$-$C_4$ alkylthio, $C_6$-$C_{12}$ arylthio, $C_7$-$C_{10}$ aralkyloxy, $C_7$-$C_{16}$ aralkyl-thio; and $R_5$ is H or $C_1$-$C_{12}$ linear or branched alkyl; $C_2$-$C_{12}$ linear or branched monoalkenyl; $C_7$-$C_{20}$ aralkyl, wherein the alkyl chain is linear or branched $C_1$-$C_8$ and the aryl moiety is $C_6$-$C_{12}$; heterocyclic alkyl wherein the alkyl chain is linear or branched $C_1$-$C_8$ and the heterocyclic ring is 5–6 membered, optionally fused with a benzene ring, fully aromatic, containing 1 to 2 of oxygen, nitrogen or sulfur as heteroatoms; $C_4$-$C_{10}$ cycloalkylalkyl; $C_3$-$C_7$ cycloalkyl; wherein the values for $R_5$ can be substituted by one or more of halo, hydroxy, carboxy, $C_1$-$C_4$ alkoxycarbonyl, $C_7$-$C_{16}$ arylalkoxycarbonyl, $C_3$-$C_7$ cycloalkyl, $C_1$-$C_4$ alkoxy, $C_6$-$C_{12}$ aryloxy, $C_3$-$C_6$ cycloalkyloxy, $C_3$-$C_6$ cycloalkylthio, amino, mono- or di- $C_1$-$C_8$ alkylamino, thio, $C_1$-$C_4$ alkylthio, $C_6$-$C_{12}$ arylthio, $C_7$-$C_{16}$ aralkylthio, or the radical —S—$(CH_2)_n$CH$(NH_2)$COOH. These compounds have dehydropeptidase (DHP) enzyme inhibitor activity.

5 Claims, No Drawings

PHOSPHOROUS CONTAINING DHP ENZYME INHIBITORS

This is a continuation of application Ser. No. 07/264,241 filed Oct. 28, 1988, now abandoned.

BACKGROUND OF THE INVENTION

1. Field of the Invention

This invention relates to new agents which inhibit renal dehydro eptidase (DHP) and, therefore, potentiate the antibiotic activity of carbapenem antibiotics.

2. Description of the Art

Renal dehydropeptidase (E.C. 3.4.13.11) is a mammalian enzyme which metabolizes carbapenem antibiotics such as thienamycin and imipenem. Inhibition of this enzyme enhances the urinary recovery of these antibiotics and reduces their renal toxicity. EPO Publication No. 0091594 to Sanraku-Ocean Co., Ltd. describes aminocarboxylic acid derivatives Possessing dipeptidase inhibiting activity. EPO Publication No. 0210545 to Merck & Co., Inc. describes renin inhibitors which are phosphinic acids similar to the instant compounds where $R_1$ is cyclohexylmethyl. The development of cilastatin as a renal dehydropeptidase inhibitor for use in combination with imipenem has been reviewed by F. M. Kahan et al., *J. Antimicrobial Chemotherapy*, 12. Suppl. D, 1-35 (1983).

U.S. Pat. No. 4,374,131 to Petrillo (assigned to E. R. Squibb & Sons, Inc.) discloses amino and substituted amino phosphinyl-alkanoyl compounds which are useful hypertensive agents due to their angiotensin-converting-enzyme (ACE) inhibition activity.

E. D. Thorsett et al., (Merck & Co., Inc.) *Proc. Natl. Acad. Sci. USA* Vol. 79, pp 2176-2180 (April 1982) discloses phosphorus containing inhibitors of angiotensin-converting enzyme.

Further, U.S. Pat. No. 4,715,994 by Parsons et al., (assigned to Merck & Co., Inc.) discloses 3-(1-aminoalkyl-propionic)-(2-substituted) phosphinic acids which display antibacterial activity and potentiate carbapenem antibiotics.

With this background, the search for newer and more effective antibacterial agents is a continuing one.

SUMMARY OF THE INVENTION

It has been found that compounds of Formulae I and II, shown below, inhibit renal dehydropeptidase E.C. (3.4.13.11) and are useful in potentiating the in vivo effects of penem and carbapenem antibiotics such as imipenem.

By this invention there is provided a method of treatment for bacterial infections which comprises administering to a host a therapeutically effective amount of a DHP-inhibiting compound of Formula I or II, in combination with a therapeutically effective amount of a carbapenem or penem antibiotic:

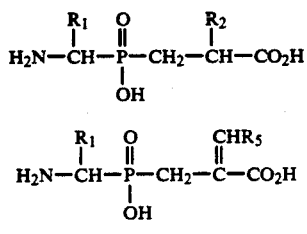

wherein:

$R_1$ is
- (a) $C_2-C_{12}$ linear or branched unsubstituted alkyl;
- (b) $C_1-C_{12}$ linear or branched substituted alkyl;
- (c) $C_2-C_{12}$ linear or branched monoalkenyl;
- (d) $C_2-C_{12}$ linear or branched alkynyl;
- (e) $C_7-C_{20}$ aralkyl, wherein the al chain is linear or branched $C_1-C_8$ and the aryl moiety is $C_6-C_{12}$;
- (f) $C_4-C_{10}$ cycloalkylalkyl;
- (g) $C_3-C_7$ cycloalkyl;

wherein said above values for $R_1$, excluding (a), can be substituted by one or more: $C_1-C_4$ alkoxy, $C_3-C_6$ cycloalkyloxy, $C_3-C_6$ cycloalkylthio, $C_6-C_{12}$ aryloxy, $C_1-C_4$ alkylthio, $C_6-C_{12}$ arylthio, $C_7-C_{10}$ aralkyloxy, $C_7-C_{16}$ aralkylthio;

$R_2$ is
- (a) H or $C_1-C_{12}$ linear or branched alkyl;
- (b) $C_2-C_{12}$ linear or branched monoalkenyl;
- (c) $C_7-C_{20}$ aralkyl, wherein the alkyl chain is linear or branched $C_1-C_8$ and the aryl moiety is $C_6-C_{12}$;
- (d) heterocyclic alkyl, wherein the alkyl chain is linear or branched $C_1-C_8$ and the heterocyclic ring is 5-6 membered, optionally fused with a benzene ring, fully aromatic, containing 1-2: O, N or S heteroatoms;
- (e) $C_4-C_{10}$ cycloalkylalkyl;
- (f) $C_3-C_7$ cycloalkyl;

wherein said above values for $R_2$ can be substituted by one or more: halo, hydroxy, carboxy, $C_1-C_4$ alkoxycarbonyl, $C_7-C_{16}$ arylalkoxycarbonyl, $C_3-C_7$ cycloalkyl, $C_1-C_4$ alkoxy, $C_6-C_{12}$ aryloxy, $C_3-C_6$ cycloalkyloxy, $C_3-C_6$ cycloalkylthio, amino, mono- or di-$C_1-C_8$ alkylamino, thio, $C_1-C_4$ alkylthio, $C_6-C_{12}$ arylthio, $C_7-C_{16}$ aralkylthio, or the radical $-S-(CH_2)_n-CH(NH_2)COOH$;

$R_5$ is
- (a) H or $C_{1-C12}$ linear or branched alkyl;
- (b) $C_2-C_{12}$ linear or branched monoalkenyl;
- (c) $C_7-C_{20}$ aralkyl, wherein the alkyl chain is linear or branched $C_1-C_8$ and the aryl moiety is $C_6-C_{12}$;
- (d) heterocyclic alkyl, wherein the alkyl chain is linear or branched $C_1-C_8$ and the heterocyclic ring is 5-6 membered, optionally fused with a benzene ring, fully aromatic, containing 1-2: O, N or S heteroatoms;
- (e) $C_4-C_{10}$ cycloalkylalkyl
- (f) $C_3-C_7$ cycloalkyl;

wherein said above values for $R_5$ can be substituted by one or more: halo, hydroxy, carboxy, $C_1-C_4$ alkoxycarbonyl, $C_7-C_{16}$ arylalkoxycarbonyl, $C_3-C_7$ cycloalkyl, $C_1-C_4$ alkoxy, $C_6-C_{12}$ aryloxy, $C_3-C_6$ cycloalkyloxy, $C_3-C_6$ cycloalkylthio, amino, mono- or di-$C_1-C_8$ alkylamino, thio, $C_1-C_4$ alkylthio, $C_6-C_{12}$ arylthio, $C_7-C_{16}$ aralkylthio, or the radical $-S-(CH_2)_n-CH(NH_2)COOH$; and including DHP-inhibiting stereoisomers and racemates thereof Structures I and II.

Further provided is a pharmaceutical composition useful in the treatment of antibacterial infections which comprises a pharmaceutically effective amount of a DHP-inhibiting compound of above-defined Formula I or II, or mixture thereof, in combination with a pharmaceutically effective amount of a carbapenem or penem antibiotic.

Further provided is a DHP-inhibiting compound of Formula I or II:

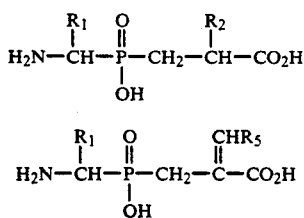

wherein:

$R_1$ is
- (a) $C_2$-$C_{12}$ linear or branched unsubstituted alkyl;
- (b) $C_2$-$C_{12}$ linear or branched substituted alkyl;
- (c) $C_2$-$C_{12}$ linear or branched monoalkenyl;
- (d) $C_2$-$C_{12}$ linear or branched alkynyl;
- (e) $C_7$-$C_{20}$ aralkyl, wherein the alkyl chain is linear or branched $C_1$-$C_8$ and the aryl moiety is $C_6$-$C_{12}$;
- (f) $C_3$-$C_7$ cycloalkyl;
- (g) $C_4$-$C_{10}$ cycloalkylalkyl, for structure II only;

wherein said above values for $R_1$, excluding (a), can be substituted by one or more: $C_1$-$C_4$ alkoxy, $C_6$-$C_{12}$ aryloxy, $C_1$-$C_4$ alkylthio, $C_6$-$C_{12}$ arylthio, $C_3$-$C_6$ cycloalkyloxy, $C_3$-$C_6$ cycloalkylthio, $C_7$-$C_{10}$ aralkyloxy, $C_7$-$C_{16}$ aralkylthio;

$R_2$ is
- (a) H or $C_1$-$C_{12}$ linear or branched alkyl;
- (b) $C_2$-$C_{12}$ linear or branched monoalkenyl;
- (c) $C_7$-$C_{20}$ aralkyl, wherein the alkyl chain is linear or branched $C_1$-$C_8$ and the aryl moiety is $C_6$-C12;
- (d) heterocyclic alkyl, wherein the alkyl chain is linear or branched $C_1$-$C_8$ and the heterocyclic ring is 5-6 membered, optionally fused with a benzene ring, fully aromatic, containing 1-2: O, N or S heteroatoms;
- (e) $C_3$-$C_7$ cycloalkyl;
- (f) $C_4$-$C_{10}$ cycloalkylalkyl;

wherein said above values for $R_2$ can be substituted by one or more: halo, hydroxy, carboxy, $C_1$-$C_4$ alkoxycarbonyl, $C_7$-$C_{16}$ arylalkoxycarbonyl, $C_3$-$C_7$ cycloalkyl, $C_1$-$C_4$ alkoxy, $C_6$-$C_{12}$ aryloxy, $C_3$-$C_6$ cycloalkyloxy, $C_3$-$C_6$ cycloalkylthio, amino, mono- or di-$C_1$-$C_8$ alkylamino, thio, $C_1$-$C_4$ alkylthio, $C_6$-$C_{12}$ arylthio, $C_7$-$C_{16}$ aralkylthio, or the radical —S—$(CH_2)_n$—CH$(NH_2)$COOH;

$R_5$ is
- (a) H or $C_1$-$C_{12}$ linear or branched alkyl;
- (b) $C_2$-$C_{12}$ linear or branched monoalkenyl;
- (c) $C_7$-$C_{20}$ aralkyl, wherein the alkyl chain is linear or branched $C_1$-$C_8$ and the aryl moiety is $C_6$-C12;
- (d) heterocyclic alkyl, wherein the alkyl chain is linear or branched $C_1$-$C_8$ and the heterocyclic ring is 5-6 membered, optionally fused with a benzene ring, fully aromatic, containing 1-2: O, N or S heteroatoms;
- (e) $C_4$-$C_{10}$ cycloalkylalkyl;
- (f) $C_3$-$C_7$ cycloalkyl;

wherein said above value for $R_5$ can be substituted by one or more: halo, hydroxy, carboxy, $C_1$-$C_4$ alkoxycarbonyl, $C_7$-$C_{16}$ arylalkoxycarbonyl, $C_3$-$C_7$ cycloalkyl, $C_1$-$C_4$ alkoxy, $C_6$-$C_{12}$ aryloxy, $C_3$-$C_6$ cycloalkyloxy, $C_3$-$C_6$ cycloalkylthio, amino, mono- or di-$C_1$-$C_8$ alkylamino, thio, $C_1$-$C_4$ alkylthio, $C_6$-$C_{12}$ arylthio, $C_7$-$C_{16}$ aralkylthio, or the radical —S—$(CH_2)_n$—CH$(NH_2)$COOH; and including DHP-inhibiting stereoisomers and racemates thereof Structures I and II.

DESCRIPTION OF THE INVENTION AND PREFERRED EMBODIMENTS

The novel claimed compounds of the above dehydropeptidase inhibitors.

The values for $R_1$ for (a) $C_2$-$C_{12}$ linear or branched unsubstituted alkyl include ethyl, propyl, isopropyl, n-butyl, isobutyl, sec-butyl, t-butyl, n-pentyl, isopentyl, n-hexyl, n-heptyl, n-octyl, iso-octyl, n-decyl, n-undecyl, n-dodecyl and the like. Preferred in this series is n-butyl, isobutyl, n-pentyl and n-hexyl.

Values for $R_1$ for (b) $C_1$-$C_{12}$ linear or branched alkyl, where substituted, include the values above for $R_1$ (a), substituted by the above-defined substituents, including the following preferred substituents: methoxy, ethoxy, propoxy, butoxy, methylthio, ethylthio, propylthio, butylthio, cyclopentyloxy, cyclopentylthio, cyclopropylthio, benzylthio, 2-phenethylthio, 2-phenethylthio and the like.

Values for $R_1$ for (e) $C_2$-$C_2$ linear or branched monoalkenyl include ethenyl, propenyl, 1-butenyl, 2-butenyl, 1-pentenyl, 2-pentenyl, 2-methyl-2-butenyl and the like.

Values for $R_1$ for (d) $C_2$-$C_{12}$ linear or branched alkynyl include: ethynyl, propynyl, 1-butynyl, 2-butynyl, 2-methyl-3-pentynyl and the like.

Values for $R_1$ for (e) $C_7$-$C_{20}$ aralkyl include benzyl, 2-phenylethyl, 1-phenylethyl, 4-methylphenyl-methyl and the like. Preferred in this series is benzyl.

Values for $R_1$ for (f) $C_4$-$C_{10}$ cycloalkylalkyl include: cyclohexylmethyl, cyclopentylmethyl, 2-cyclohexylethyl, 2-cyclooctylethyl, and the like. Preferred in this series is cyclopentylmethyl and cyclohexylmethyl.

The method of use and pharmaceutical composition claims include the compounds of Formulas I and II where $R_1$ is cyclohexylmethyl whereas the new compound claims of Structure I do not.

Values for $R_1$ for (g) $C_3$-$C_7$ cycloalkyl include: cyclopropyl, cyclobutyl, cyclopentyl, cyclohexyl, and the like. Preferred in this series is cyclopentyl and cyclohexyl.

Preferred substituent values for $R_1$ include: methoxy, ethoxy, phenoxy, methylthio, ethylthio, phenylthio, benzyloxy, 2-phenylethyloxy, benzylthio, 2-phenylethylthio, and the like.

The values of the alkyl, alkenyl groups for $R_2$ and $R_5$, except where noted otherwise, represented by any of the variables include linear or branched, alkyl and monoalkenyl and chain hydrocarbon radicals from two to twelve carbon atoms, for example, ethyl, n-propyl, isopropyl, n-butyl, isobutyl, sec-butyl, t-butyl, n-pentyl, isopentyl, n-heptyl, n-nonyl, 4,4-dimethylpentyl, or vinyl, allyl, 1-butenyl, 2-butenyl, 5-hexenyl and the like. Preferred are isopropyl, n-butyl, n-pentyl, n-heptyl or 1-butenyl.

Values of $C_3$-$C_7$ cycloalkyl and $C_4$-$C_{10}$ cycloalkylalkyl include: cyclopentyl, cyclohexyl, cyclopentylmethyl, cyclopentylethyl, cyclohexylmethyl, cyclohexylethyl, cyclopropyl, and the like.

The aralkyl group represented by the above variables has from one to eight carbon atoms in the alkyl portion and "aryl" where noted, represents phenyl, naphthyl, or biphenyl. Representative examples include benzyl, phenethyl, 4-phenyl-n-butyl, 1-phenyl-n-octyl, and the like.

The aromatic heterocyclic, i.e. "heteroaryl" substituent, are synonymous, and recited above represents a 5- or 6-membered aromatic ring containing from one to three O, N or S heteroatoms, preferably one O or S and/or 1-3N heteroatoms, such as, for example, pyridyl, thienyl, furyl, imidazolyl, and thiazolyl as well as any bicyclic group derivable therefrom in which any of the above heterocyclic rings is fused to a benzene ring such as, for example, indolyl, quinolinyl, isoquinolinyl, benzimidazolyl, benzothiazolyl, benzofuryl, and benzothienyl.

The named substituents on the $R_2$ and $R_5$ alkyl and alkenyl chains can be present on the aromatic rings in the aralkyl, heterocyclic alkyl and heteroaryl groupings as well. Site of substitution includes all available sites and substitution can involve one or more of the same or different groups.

The substituents are: halo, meaning fluoro, chloro, bromo or iodo; hydroxy; carboxy; $C_1$-$C_4$ linear or branched alkoxycarboxy, e.g. methoxycarbonyl and ethoxycabonyl; $C_7$-$C_{16}$ arylalkoxy carbonyl, e.g. benzyloxycarbonyl, n-butyloxycarbonyl; $C_3$-$C_7$ cycloalkyl, e.g. cyclopentyl and cyclohexyl; $C_1$-$C_4$ alkoxy, e.g. t-butoxy and ethoxy; $C_6$-$C_{12}$ aryloxy, e.g. biphenyloxy, benzyloxy; amino; mono- or di-$C_1$-$C_8$ dialkylamino, e.g. methylamino, isopropylamino, n-butylamino, isohexylamino, N,N-diethylamino, methylethylamino, methyl-t-butylamino, di-n-octylamino; thio; $C_1$-$C_4$ alkylthio, e.g. methylthio, ethylthio $C_6$-$C_{12}$ arylthio, e.g. phenylthio; $C_7$-$C_{16}$ aralkylthio, e.g. benzylthio, naphthylmethylthio; the radicals —S—$CH_2$—$CH(NH_2)COOH$ and —S—$(CH_2)_2$—$CH(NH_2)COOH$, both preferably in the L-configuration; and, where a thio substituent is present, $R_2$/$R_5$ must be at least a $C_2$ alkyl grouping. Where an aryl or heteroaryl group is present in the substituent, the ring carbons can additionally be substituted by one or more of linear or branched $C_1$-$C_4$ alkyl, e.g. methyl, ethyl, isopropyl, t-butyl; trihalomethyl, "halo" having the same meaning as described above, e.g. trichloromethyl, trifluoromethyl; nitro, cyano or sulfonamide.

Preferred are the compounds wherein:
$R_1$ is cyclohexylmethyl, cyclopentylmethyl, n-pentyl, n-butyl, n-hexyl, isobutyl,
$R_2$ and $R_5$ are:
  $C_3$-$C_7$ cycloalkyl;
  $C_1$-$C_{10}$ linear or branched alkyl, substituted or unsubstituted;
  $C_7$-$C_{14}$ aralkyl, substituted or unsubstituted.
  wherein these groups can be substituted with halo, amino, mono- or di-$C_1$-$C_4$ linear or branched alkylamino, carboxyl, $C_1$-$C_4$ alkoxycarbonyl, hydroxy, $C_1$-$C_4$ alkoxy, $C_5$-$C_6$ cycloalkyl, $C_6$-$C_{10}$ aryloxy, thio, $C_1$-$C_4$ linear or branched alkylthio, $C_6$-$C_{10}$ arylthio, $C_7$-$C_{14}$ aralkylthio, —S—$(CH_2)_n$—$CH(NH_2)CO_2H$; wherein the aryl group ring carbons can further be substituted by linear or branched $C_1$-$C_4$ alkyl; $R_3$ and $R_4$ are hydrogen, $C_1$-$C_4$ linear or branched alkyl e.g. methyl, ethyl, or $C_7$-$C_{14}$ aralkyl e.g. benzyl.

The preferred compounds of Structures I or II, for use as DHP inhibiting agents include those having the carbon attached to $R_1$ in the (R) or (RS) configuration preferably (R), and the carbon attached to $R_2$ in the (R) (RS) or (S) configuration, preferably (RS) or (S) and if $R_5$ is present, the double bond is preferred in the Z configuration.

The Formulas I and II compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionafe, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine and N-methyl-D-glucamine, and salts with amino acids such as arginine, lysine, and so forth. Water or oil-soluble or dispersible products are thereby obtained.

The pharmaceutical compositions herein useful in the treatment of antibacterial infections comprise a pharmaceutically effective amount of a compound of Formula I or II, or mixture thereof, in combination with a pharmaceutically effective amount of a carbapenem or penem antibiotic.

By the term "carbapenem" or "penem" antibiotic as used herein is meant those carbapenems and penems which are known in the art as possessing antibacterial activity. Inclusive therein are those carbapenems and penems described in U.S. Pat. No. 4,539,208 to F. M. Kahan and H. Kropp, and EPO Publication No. 0,161,546, both assigned to Merck & Co., Inc., hereby incorporated by reference, those specifically listed in the Merck Index, Tenth Edition, i.e., imipenem and 3-]2-dimethylaminocarbonyl tetrahydro-pyrrolidin-4-yl]thio-6-(1-hydroethyl)-7-oxo-1-azabicyclo-[3.2.0]hept-2-ene-2-carboxylic acid (Sumitomo).

Specifically preferred DHP-inhibiting compounds useful in the composition include:
1. 1-Amino-3-methylbutyl-[2-carboxy-1-hexyl]phosphinic acid
2. 1-Aminopropyl-[2-carboxy-4-phenyl-1-butyl]phosphinic acid
3. 1-Aminopropyl-[2-carboxy-1-butyl]phosphinic acid
4. 1-Aminopropyl-[2-carboxy-1-hexyl]phosphinic acid
5. 1-Aminopropyl-2-phenylethyl-[2-carboxy-1-hexyl]-phosphinic acid
6. (1-Amino-2-cyclohexylethyl)-2-carboxy-5-(4-pyridyl)-pentyl phosphinic acid
7. 1-Amino-2-cyclohexylethyl-[2-carboxy-5-(4-methyl)-1-pentyl phosphinic acid
8;9. (1-Amino-2-cyclohexylethyl)-2-carboxy-4-methyl-(E & Z)-2-butenyl phosphinic acids
10. (1-Amino-2-cyclohexylethyl)-2-carboxy-3(Z)-cyclohexyl-2-butenyl phosphinic acid
11. (1-Amino-2-cyclohexylethyl)-2-carboxy-3-cyclohexyl-1-propyl phosphinic acid
12. (1-Aminohexyl)-2-carboxy-2(Z)-octenyl phosphinic acid
13. (1-Amino-1-hexyl)-2-carboxy-1-octyl phosphinic acid
14. (1-Aminohexyl)-2-carboxyl-4-cyclopentyl-2(Z)-butenyl phosphinic acid
15. (1-Amino-1-hexyl)-2-carboxy-4-cyclopentyl-1-butyl phosphinic acid
16. (1-Amino-2-cyclohexylethyl)-2-carboxy-2-(Z)-octenyl phosphinic acid
17. (1-Amino-2-cyclohexylethyl)-2-carboxy-1-octenyl phosphinic acid 18. (1-Amino-2-cyclohexylethyl)-2-carboxy-4-cyclopentyl-2(Z)-butenyl phosphinic acid
19. (1-Amino-2-cyclohexylethyl)-2-carboxy-4-cyclopentyl-1-butylphosphinic acid
20. (1-Aminohexyl)-2-carboxy-3-cyclohexyl-2(Z)-butenyl phosphinic acid
21. (1-Amino-1-hexyl)-2-carboxy-3-cyclohexyl-1-propyl phosphinic acid
22. [1(R)-Amino-2-cyclohexylethyl]-2-carboxy-4-methyl-2-(Z)-butylphosphinic acid
23. [1-(R)-Amino-2-cyclohexylethyl]-2-carboxy-3(Z)-cyclohexyl-2-propenyl phosphinic acid
24. [1-(R)-Amino-2-cyclohexylethyl]-2-carboxy-4-cyclopentyl-2(Z)-butenylphosphinic acid.

Also provided is a method for treating a bacterial infection in a mammalism host comprising administering to said host a therapeutically effective amount of the above-described composition containing a compound of Formula I or II or mixture thereof.

Compounds of this invention inhibit dehydropeptidase-I (renal dipeptidase, ED 3.4.13.11) and, therefore, potentiate the antibiotic activity of carbapenem antibiotics. Renal dehydropeptidase activity was first described by M. Bergmann and H. Schleich, Z. Physiol. Chem., 205, 65 (1932); see also B. J. Campbell et al., Biochem. Biophys. Acta, 118, 371 (1966) and references therein.

In order to demonstrate the ability of the compounds of Formula I to suppress the action of the renal dipeptidase enzyme, an in vitro screen procedure was followed. This measured the ability of compounds to inhibit hydrolysis of glycyldehydrophenylalanine (GDP) by a solubilized preparation of dipeptides isolated from hog kidneys. The procedure is as follows: to a 1 ml system containing 50 mM "MOPS" (3-(N-morpholino)-propanesulfonic acid) buffer, pH 7.1 is added 5 mg of lyophilized enzyme, and the test compound at a final concentration of 0.1 mM. After a five minute incubation of 37° C., GDP is added to a final concentration of 0.05 mM. Incubation is continued for 10 minutes, at 37° C. and hydrolysis of GDP is measured by the change in optical density with time at 275 nm. Inhibition of the enzyme is gauged by comparison to a standard run containing no inhibitor and is expressed as the inhibitor binding constant K. This is the concentration of the inhibitor which achieves 50% inhibition of enzyme.

The tables below summarize some representative data with compounds of this invention.

TABLE I
RENAL DEHYDROPEPTIDASE I INHIBITION

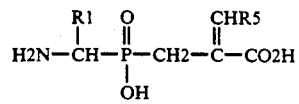

| $R_1$ | $R_5$ | Configuration at $R_1$ | Olefin Geometry | $K_i$ (nM) |
|---|---|---|---|---|
| $(CH_3)_2CHCH_2$ | $CH_3(CH_2)_3$ | RS | Z | 1.6 |
| $CH_3(CH_2)_4$ | cyclo-$C_6H_{11}$ | RS | Z | 0.5 |
| $CH_3(CH_2)_4$ | $CH_3(CH_2)_4$ | RS | Z | 1.4 |
| $PhCH_2$ | $CH_3(CH_2)_4$ | RS | Z | 68 |
| (cyclo-$C_6H_{11}$)$CH_2$ | $(CH_3)_2CH$ | RS | Z | 2.1 |
| (cyclo-$C_6H_{11}$)$CH_2$ | $(CH_3)_2CH$ | RS | E | 21 |
| (cyclo-$C_6H_{11}$)$CH_2$ | $(CH_3)_2CH$ | R | Z | 0.54 |
| (cyclo-$C_6H_{11}$)$CH_2$ | $CH_3(CH_2)_4$ | RS | Z | 3.1 |
| (cyclo-$C_6H_{11}$)$CH_2$ | cyclo-$C_6H_{11}$ | RS | Z | 0.9 |
| (cyclo-$C_6H_{11}$)$CH_2$ | (cyclo-$C_5H_9$)$CH_2$ | R | Z | 0.86 |

TABLE I-continued
RENAL DEHYDROPEPTIDASE I INHIBITION

| $R_1$ | $R_5$ | Configuration at $R_1$ | Olefin Geometry | $K_i$ (nM) |
|---|---|---|---|---|
| (cyclo-$C_6H_{11}$)$CH_2$ | cyclo-$C_6H_{11}$ | R | Z | 0.52 |

TABLE II

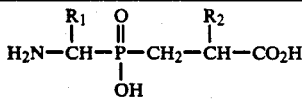

| $R_1$ | $R_2$ | Configuration at $R_1$ | Configuration at $R_2$ | $K_i$ (nM) |
|---|---|---|---|---|
| $CH_3CH_2$ | $Ph(CH_2)_2$ | RS | RS | 6.8 |
| $CH_3CH_2$ | $CH_3CH_2$ | RS | RS | 1.3 |
| $CH_3CH_2$ | $CH_3(CH_2)_3$ | RS | RS | 2.3 |
| $(CH_3)_2CHCH_2$ | $CH_3(CH_2)_3$ | RS | RS | 2.4 |
| $PhCH_2$ | $CH_3(CH_2)_3$ | RS | RS | 84 |
| $CH_3(CH_2)_4$ | $CH_3(CH_2)_5$ | RS | RS | 8.0 |
| $CH_3(CH_2)_4$ | (cyclo-$C_5H_9$)$CH_2CH_2$ | RS | RS | 7.0 |
| $CH_3(CH_2)_4$ | (cyclo-$C_6H_{11}$)$CH_2$ | RS | RS | 9.7 |
| (cyclo-$C_6H_{11}$)$CH_2$ | $CH_3(CH_2)_5$ | RS | RS | 1.6 |
| (cyclo-$C_6H_{11}$)$CH_2$ | (cyclo-$C_5H_9$)$CH_2CH_2$ | R | RS | 2.7 |
| (cyclo-$C_6H_{11}$)$CH_2$ | (cyclo-$C_6H_{11}$)$CH_2$ | R | RS | 0.5 |
| (cyclo-$C_6H_{11}$)$CH_2$ | $(CH_2)_3$-pyridin-4-yl | R | RS | 4.0 |

The in vivo effectiveness of DHP inhibitors to increase the metabolic stability of carbapenem antibiotics can be demonstrated by measuring the urinary recovery of such antibiotics in the presence and absence of coadministered dehydropeptidase inhibitor. For example, see F. M. Kahan et al., J. Antimicrobial Chemotherapy, 12, Suppl. D, 1-35 (1983). It is also possible to observe this potentiation by measuring the dosage required to treat infections in animals with a dehydropeptidase susceptible antibiotic alone or in combination with a dehydropeptidase inhibitor.

For administration, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the compounds of the invention.

The present compositions can be administered parenterally and this is preferred when they are used in combination with a carbapenem antibiotic such as imipenem. They may also be administered orally. The compounds of this invention may also be used to treat topical antibacterial infection. Therefore, these compounds may be presented in a number of appropriate dosage forms; e.g., tablets, capsules, suspensions, solutions, and the like, for oral administration; solutions, suspensions, emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1)inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy beam and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

For topical use, creams, ointments, jellies, solutions or suspensions, etc., containing the compositions of the invention are employed.

Treatment dosage for human beings can be varied as necessary. Generally, oral dosages of the antibacterial compounds of this invention when given orally are in the range 250 mg to 4 g per patient given 3-4 times daily. The intravenous or intramuscular dosages are 100 mg to 1 g given 3-4 times daily. When the compounds of the invention are given intravenously or intramuscularly to potentiate carbapenem antibiotics such as imipenem they are given in combination with the antibiotic in amounts of 0.1-10 mg/kg/day.

The amount of active ingredient that may be combined with the carrier materials to produce a single dosage form will vary depending upon the host treated and the particular mode of administration. For example, a formulation intended for oral administration may contain, for example, from 100 mg to 2000 mg of active agent compounded with an appropriate and convenient amount of carrier material which may vary from about 5 to about 95 percent of the total composition.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of Formula I can be prepared by the methods shown in the following Reaction Schemes wherein $R^1$ and $R^2$ are as defined above unless otherwise indicated.

As will be evident to those skilled in the art and as demonstrated in the Examples hereinafter, reactive groups not involved in the reactions, such as amino, carboxy, mercapto, etc., may be protected by methods standard in peptide chemistry prior to the coupling reactions and subsequently deprotected to obtain the desired products. Cbz refers to carbobenzyloxy, and BOC refers to t-butoxycarbonyl.

from both the optically active and racemic materials are claimed in the present invention.

The protected aminoalkylphosphonous acid (1) is esterified with either diazomethane or triethylorthoformate to give the methyl or ethyl ester (2) which is deprotonated with either sodium methoxide or ethoxide in the corresponding alcohol and treated with the appropriately substituted acrylate to give (4), the protected form of Formula I. The acrylates can be prepared by procedures outlined by J. Harley-Mason in tetrahedron 36, 1036-1070 (1980), hereby incorporated by reference.

Compound 4 can be alternatively synthesized by alkylation of the protected aminoalkylphosphonous acid (1) with appropriately substituted 3-halopropionates or acrylates in the presence of a trialkylsilylchloride such as trimethylsilylchloride and a tertiary amine such as triethylamine according to the general methods of J. K. Thottathil et al. (*Tetrahedrom Lett.* 25, 4737-40, 4741-44 (1984), hereby incorporated b reference.

The phosphinc acid 3 may be esterified by diazomethane to give compound 4.

REACTION SCHEME A:

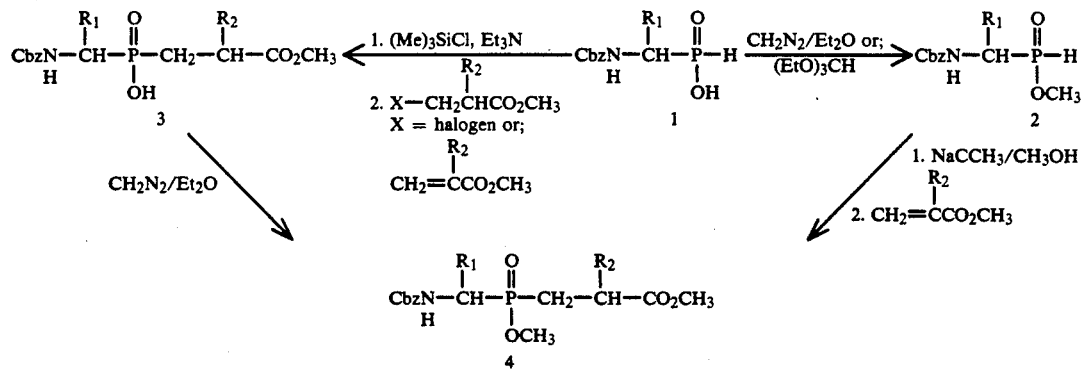

REACTION SCHEME B:

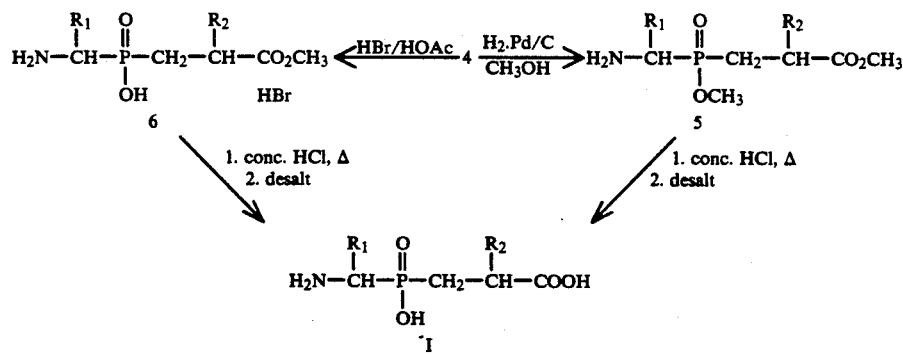

The Cbz aminoalkylphosphonous acids (1) in Reaction Scheme A can be prepared according to procedures described by P. A. Bartlett et al. (*J. Amer. Chem. Soc.* 106, 4282-4283 (1984) and E. K. Baylis et al. (*J. Chem. Soc. Perkin Trans.* 1, 2845-2853 (1984) and can be resolved to give optically active materials by the method of Baylis (reference above) both methods hereby incorporated by reference. Compounds derived As illustrated in Reaction Scheme B, Compound 4 is converted to formula I by two standard routes. The carbobenzyloxy group can be removed by either hydrogenation in an alcohol such as ethanol with a catalyst such as Pd/C, or by cleavage with HBr in acetic acid. Subsequent ester hydrolysis in concentrated HCl provides, after treating with propylene oxide, for example, compounds of formula I.

REACTION SCHEME C:

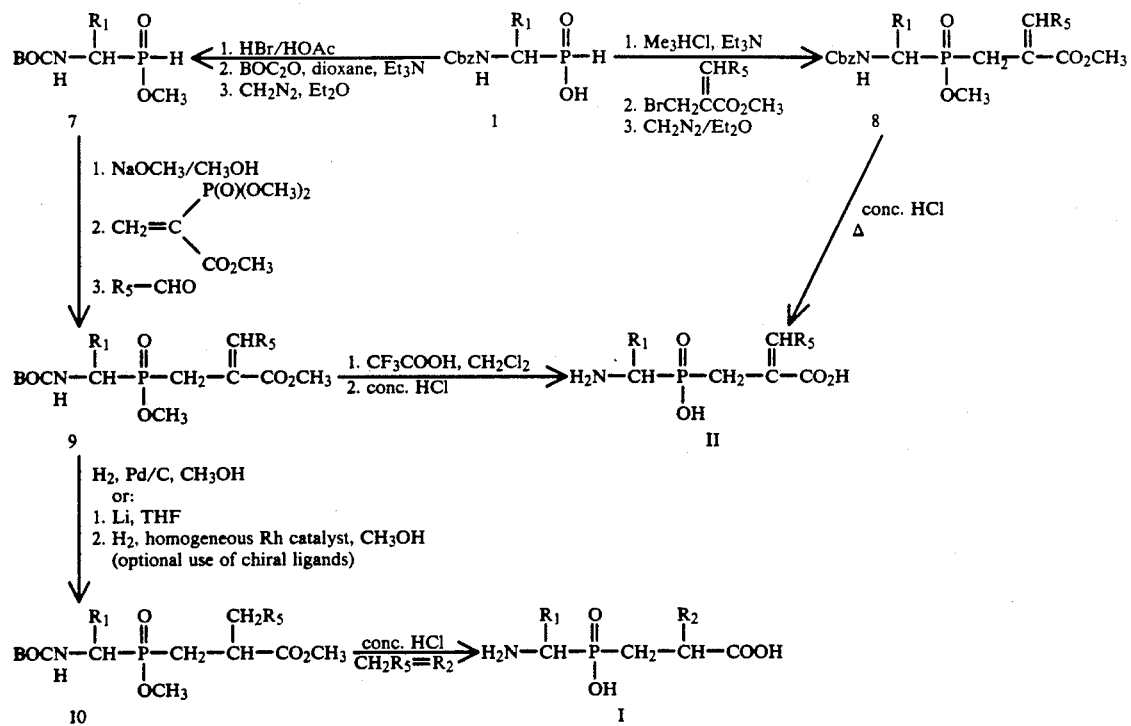

Reaction Scheme C illustrates an alternative route involving a conjugate addition of the phosphonous ester under the conditions previously outlined to trimethyl-2-phosphonoacrylate. The subsequent anion is then trapped with an aldehyde yielding the dehydro compound 9, as a mixture of E and Z isomers. A similar intermediate 8 can be prepared by alkylation of the protected aminoalkylphosphonous acid with substituted 2-bromomethylacrylates under conditions reported by J. K. Thottathil, et al. Tetrahedron Lett. 25, 4737–40, 4741–44 (1984), hereby incorporated by reference. Treatment of either 8 or 9 under acidic conditions then yields compounds of Formula II. Alternatively, olefin 9 may be selectively reduced using homogenous catalysis. For instance, one may use a [(COD)RhCl]$_2$ complex with an organophosphine ligand in methanol to give compound I which can be further elaborated by procedures already outlined.

Chiral organophosphine ligands such as (−)2,3-0-isopropylidene-2,3-dihydroxy-1,4-bis (diphenylphosphino)butane, ((−) DIOP), may be used in order to produce the S or R stereoisomers at R$_2$ in high enantiomeric excess.

Preferred diastereomers for dehydropeptidase inhibition correspond to L-amino acids (R stereochemistry) at the carbon bearing R$_1$. Stereochemistry at R$_2$ may correspond to either D- or L-amino acids for good activity (R or S). The stereochemistry at R$_5$ in dehydro analogs can be either E or Z and preferably is Z.

Melting points were recorded on a Thomas-Hoover melting point apparatus and are uncorrected as are all boiling points. $_1$H NMR spectra were taken on a Varian XL-300 FT spectrometer. Chemical shifts are reported in ppm downfield from tetramethylsilane as internal standard. IR spectra were recorded on a Perkin-Elmer Model 297 spectrometer. Optical rotations were measured with a Perkin Elmer 141 automatic polarimeter in the solvents indicated. Mass spectra (MS) were taken on a Varian 731 spectrometer at 70 eV. Those marked FAB were taken by using the fast atom bombardment method.

The following Examples are illustrations of carrying out the instant invention and should not be construed to limitation on the scope or spirit of the claimed invention.

EXAMPLE 1

Cyclohexylacetaldehyde

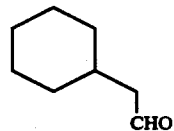

A suspension of 100 g (0.46 moles) of pyridinium chlorochromate and 100 g of celite in 800 ml of methylene chloride was stirred vigorously while 38 g (0.3 moles) of 2-cyclohexylethanol in 200 ml of methylene chloride was added all at once. The reaction turned dark immediately and became mildly exothermic. After 1 hour, 1000 ml of ether was added and the reaction mixture was filtered through a bed of silica gel (ca. 250 g) on a fritted glass disk. The pad was rinsed with an additional liter of ether. The combined filtrates were reduced in volume to approximately 200 ml and the solution was washed with 2×40 ml of 6N HCl, 1×50 ml of saturated sodium bicarbonate, and 1×50 ml of saturated NaCl solution. The organic layer was dried over magnesium sulfate, filtered and evaporated in vacuo to give a light green oil. The residue was distilled in vacuo to afford 21 g (56%) of a colorless oil (bp 74°-76° C. at 23 mm of Hg).

Product spectra: NMR (CDCl₃) (60 MHz: 0.8–2.1 (m, 121H); 2.2–2.4 (m, 2H); 9.6 (t, J=2 Hz, 1H) ppm.

EXAMPLE 2

1-Amino-2-cyclohexylethylphosphonous acid

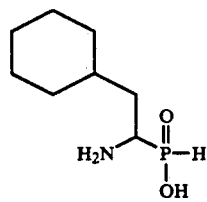

A stirred slurry of 26.00 g (0.118 moles) of aminodiphenylmethane-HCl in 100 ml of absolute ethanol was treated with 15.50 g (0.123 moles) of cyclohexylacetaldehyde, immediately followed by 12.8 ml (0.123 moles) of hypophosphorous acid (50% aqueous). The reaction mixture was heated in an oil bath held at 100° C. As the reaction approached reflux it became homogeneous, then heterogeneous again after approximately 5 minutes (white precipitate). After 45 minutes at reflux, an additional 100 ml of ethanol was added to the very thick slurry. Reflux was continued for an additional 3 hours 15 minutes. At this time the reaction mixture was cooled to 0° C. in an ice bath, then the solid filtered off. The white solid was washed with 50 ml of ice-cold ethanol and air dried.

The white solid was added to 150 ml of glacial acetic acid and 150 ml of 48% aqueous HBr added. Dissolution occurred over a period of 5 minutes, and the reaction turned a light yellow color. After another 10 minutes a white solid precipitated out of solution. Stirring at room temperature was continued for a total of 2 hours. The flask was then immersed in an oil bath preheated to 115° C. After 1 hour the reaction was almost homogeneous. After a total of 3 hours at 115° C., the reaction mixture was cooled to 0° C. in an ice bath. The solution was washed with 1×200 ml and 2×100 ml of hexanes. The hexanes wash was discarded and the remaining aqueous acid solution was evaporated to dryness on a rotary evaporator. The resulting semi-crystalline foam was dissolved in 125 ml of absolute ethanol and cooled to 0° C. in an ice bath. Propylene oxide (50 ml) was slowly added and a white precipitate was formed. The reaction mixture was allowed to warm to room temperature of its own accord while stirring. After a total of 18 hours, the slurry was cooled to 0° C. again, and the solid filtered off. The solid was washed with 100 ml more of ice-cold ethanol and dried to afford 11 98 g (53% overall) of a white solid mp 220°-221° C. (turns orange and bubbles).

Product spectra: NMR (D₂O) (60 MHz): 0.8–2.1 (m, 14H); 3.3 (m, 2H); 7.0 (d, J=527 Hz, 1H) ppm.

EXAMPLE 3

Methyl N-CBZ-1-Amino-2-cyclohexylethylphosphinate

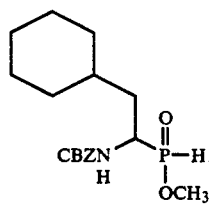

A solution of 7.00 g (0.037 moles) of 1-amino-2-cyclohexylethylphosphonous acid in 105 ml of dioxane and 40 ml of 1N NaOH was cooled to 0° C. in an ice bath and stirred vigorously while 10.50 ml (12.53 g; 0.073 moles) of benzyl chloroformate and 80 ml of 1N NaOH were added rapidly and simultaneously over a period of approximately 1 minute. The pH was adjusted to the 8-9 range using 1N NaOH (hydrion paper) added in small increments. The reaction mixture was allowed to come to room temperature, and vigorous stirring was continued for 48 hours. The dioxane was removed in vacuo and the aqueous washed with 100 ml of ether. The ether layer was discarded and the aqueous solution acidified using 1N KHSO₄ to approximately pH=1-2 (hydrion paper). The solution was extracted with 5×100 ml of ethyl acetate. The combined ethyl acetate layers were dried over anhydrous Na₂SO₄, filtered, and evaporated in vacuo to afford N-CBZ-1-amino-2-cyclohexylethylphosphonous acid as a white solid.

The solid was redissolved in 200 ml of ethyl acetate and 150 ml of ethereal diazomethane was added all at once. The reaction was stirred at room temperature for 1 hour, at which time the volatiles were removed completely vacuo to give a viscous oil. This material was crystallized using 200 ml of 1:1 ether:petroleum ether to afford 3.45 g of product. The mother liquors obtained after evaporation of the filtrate were chromatographed on silica gel using 18:1:1 methylene chloride:acetone:methanol to give an additional 5.69 g of product. Total product=9.14 g (73%).

Product spectra: NMR (CDCl₃) (60 MHz): 0.8–2.2 (m, 14H); 3.6, 3.8 (s, 3H); 3.8–4.6 (br, 1H); 5.2 (s, 2H); 6.9 (d, J=542 Hz, 1H); 7.2 (s, 5H) ppm.

EXAMPLE 4

Methyl N-BOC-1-amino-2-cyclohexylethylphosphinate

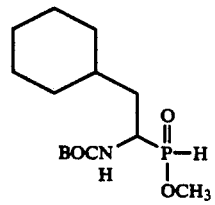

A solution of 0.955 g (0.005 moles) of 1-amino-2-cyclohexylethylphosphonous acid (Example 2) in 10 ml of dioxane and 10 ml of 0.5N NaOH was cooled to 0° C. in an ice bath. The reaction mixture was vigorously stirred while 1.26 ml (1.20 g; 0.0055 moles) of di-tert-butyldicarbonate was added all at once. The reaction mixture was allowed to come to room temperature. After a total reaction time of 17 hours, the dioxane was removed in vacuo, residue redissolved in 50 ml water and washed several times with ether. The aqueous layer was separated, cooled to 0° and acidified with 1N. The mixture extracted with 3×50 ml of ethyl acetate. The combined ethyl acetate solution was dried (anhydrous Na₂SO₄) and evaporated in vacuo to a slightly cloudy oil.

The oil was redissolved in 50 ml of ethyl acetate and treated with 50 ml of ethereal diazomethane solution. The reaction mixture was stirred at room temperature for 2 hours, then the volatiles were removed completely in vacuo to give a thick oil. The crude product was chromatographed on silica gel using 18:1:1 methylene chloride:acetone:methanol as the eluant to give 1.17 g (100%) of product as a very thick oil.

Product spectra: NMR (CDCl₃) (60 MHz): 0.0-2.2 (m containing 9H s at 1.5, 23H (total)); 3.7, 3.9 (s, 3H); 5.2-6.0 (m, 1H); 6.9 (d, J=552 Hz, 1H) ppm.

EXAMPLE 4A

Methyl-N-BOC(1R)amino-2-cyclohexylethylphosphinate

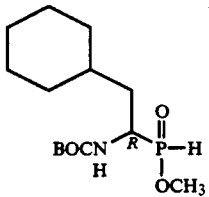

Racemic N-CBZ-1-amino-2-cyclohexylethylphosphonous acid (Example 3) was resolved to give the 1(R) ("L") isomer by the method described by E. K. Baylis, et al, *J. Chem. Soc. Perkin Trans.* 1, 2845-2853 (1984).

5.0 g (15.4 mmol) of N-CBZ-1-(R)-amino-2-cyclohexylethylphosphonous acid was treated with 10 mL of 30% hydrobromic acid in acetic acid at room temperature for 2 hours. The mixture was diluted with water and washed with 1:1 ether-ethyl acetate. The aqueous layer was removed, filtered through Celite, and volatiles removed under vacuum. The residue was redissolved in 10 mL methanol and treated with 8.6 mL (61.6 mmol) of triethylamine and 6.1 mL (26.4 mmol) of di-t-butyl-dicarbonate. After 14 hours at room temperature, the mixture was diluted with water and washed with ether. The aqueous layer was cooled to 0°, acidified to pH 2 by dropwise addition of 6N HCl, and quickly extracted several times with ether. The combined extracts were washed with brine, dried over MgSO₄, filtered and solvents removed under vacuum to afford 3.45 g (11.8 mmol, 77%) of the intermediate N-BOC-1(R)-amino-2-cyclohexylethylphosphonous acid as a white powdery foam.

A solution of 0.519 g (1.78 mmol) of this intermediate in 2 mL methylene chloride at room temperature was treated with ethereal diazomethane until a yellow color persisted. Excess reagent was quenched by dropwise addition of glacial acetic acid. All volatiles were removed under vacuum and the residue purified by medium pressure liquid chromatography on silica, eluting with ethyl acetate/acetonitrile (9:1). The title compound (0.539 g, 1.77 mmol, 99%) was thus obtained as a colorless gum.

By methods outlined in Examples, 2, 3, 4, 4A were analogously prepared:

Methyl-1-Cbz-amino-3-methylbutylphosphinate

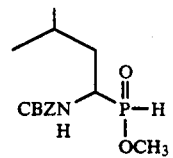

Methyl-1-Cbz-amino-n-propylphosphinate

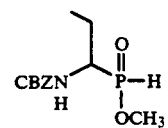

Methyl-1-Cbz-amino-2-phenylethylphosphinate

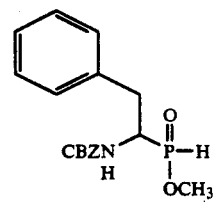

Methyl-1-Boc-amino-n-hexylphosphinate

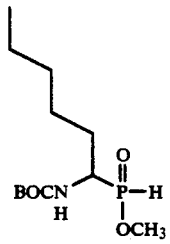

EXAMPLE 5

Methyl (N-CBZ-1-amino-2-cyclohexylethyl) 2-carbomethoxy-4-methylpentylphosphinate

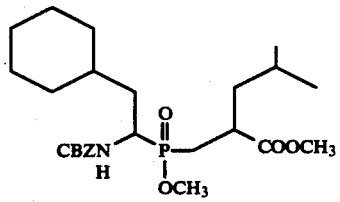

A solution of 2.75 g 0.008 moles) of methyl 1-CBZ-amino-2-cyclohexylethylphosphinate in 25 ml of absolute methanol was cooled to 0° C. in an ice bath and 4.60 ml of 2M NaOMe in methanol (0.009 moles) was added via syringe. The reaction mixture was stirred at 0° C. for 10 minutes, at which time 1.21 g (0.009 moles) of methyl 2-(2-methylpropyl)acrylate was added all at once. The reaction was allowed to proceed at 0° C. for 30 minutes, then the ice bath was removed and the reaction was allowed to proceed at room temperature for 18 hours. The methanol was removed in vacuo and the residue treated with 100 ml of 1N HCl. The aqueous was extracted with 3×50 ml of ethyl acetate. The combined ethyl acetate was dried over anhydrous MgSO₄, filtered, and evaporated in vacuo to give a colorless oil. The crude product was chromatographed on silica gel using 18:1:1 methylene chloride:acetone:methanol as the eluant to afford 1.91 g (49%) of the product as a white solid.

Product spectra: NMR (CDCl$_3$) (60 MHz): 0.8–2.2 (m, 14H); 3.6, 3.8 (s, 3H); 5.1 (s, 2H); 7.0 (d, J=535 Hz, 1H); 7.3 (s, 5H) ppm.

EXAMPLE 6

Methyl (N-BOC-1-amino-2-cyclohexylethyl) 2-carbomethoxy-4-methylpentylphosphinate

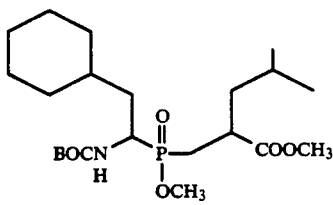

A solution of 4.85 g (0.021 moles of the ester from Example 4 in 35 ml of absolute methanol was cooled to 0° C., whereupon 11.45 ml of 2N NaOMe in methanol (0.023 moles) was added via syringe. The reaction was stirred for 10 minutes, at which time 3.10 g (0.022 moles) of methyl 2-(2-methylpropyl)acrylate was added all at once. Stirring was continued at 0° C. for 30 minutes, then the ice bath was removed and stirring was continued at room temperature for 19 hours. At that time the methanol was removed in vacuo and the residue treated with 200 ml of 1N HCl. The aqueous was extracted with 3×50 ml of ethyl acetate. The combined ethyl acetate washes were dried (MgSO$_4$), filtered and the volatiles evaporated vacuo to give an oil. The crude product was purified by silica gel chromatography using ethyl acetate as an eluant to afford 4.77 g (61%) of the product as a very viscous oil.

Product Spectra: NMR (CDCl$_3$) (60 MHz): 0.9 (m, 6H); 0.8–2.2 (m, containing 9H s at 1.5, 29H total); 3.6, 3.8 (s, 3H); 3.7 (s, 3H) ppm.

EXAMPLE 7

Methyl (1-amino-2-cyclohexylethyl) 2-carbomethoxy-4methylpentylphosphinate

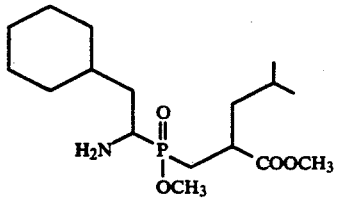

A mixture of 1.86 g (0.004 moles) of the ester product of Example 5 and 0.95 g of 10% Pd on carbon in 30 ml of absolute methanol was hydrogenated on a Parr type apparatus at 40 psig of hydrogen for 20 hours. The reaction mixture was filtered through a small pad of celite and the pad washed well with methanol. The filtrate was evaporated completely in vacuo to afford the pure free amine (1.34 g; 100%) as a viscous oil.

Product spectra: NMR (CDCl$_3$) (300 MHz) 0.8–1.0 (m, 6H); 0.8–3.0 (m, 20H); 3.7–4.0 (series of s, total 6H); 8.1 (very br s, 2H) ppm.

EXAMPLE 8

1-Amino-3-methylbutyl-[2-carboxy-1-hexyl]phosphinic acid

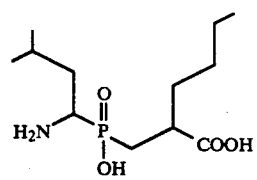

To a stirred solution of 0.4 gm (0.00134 mol) of methyl-1-N-Cbz-amino-3-methylbutylphosphinate (example 6) in 2 ml of methanol at 0° C. was added a solution of sodium methoxide in methanol (0.74 ml of a 2N solution) dropwise over 10 minutes, whereupon, was added methyl-n-butyl acrylate (0.21 ml, 0.00134 ml). The reaction was stirred 30 min at 0° C. and 3 hr at room temperature, whereupon, it was diluted with 1N HCl. The mixture was extracted twice with ethyl acetate and the combined organic fractions were dried over sodium sulfate, filtered through magnesium sulfate, and evaporated in vacuo. The product mixture was purified by chromatography (silica, ethyl aceteate) to give 0.24 gm of methyl-1-N-Cbz-amino-3-methylbutyl-[2-carbomethoxy-1-hexyl]phosphinate.

Product spectra:

TLC (silica, ethyl acetate) R$_f$=0.8

NMR (CDCl$_3$) 0.8–1.1(m,9H); 1.1–1.4(m, 5H); 1.4–1.9(m, 9H); 2.15–2.3(m, 1H); 2.7–2.9(m,1H); 3.6–3.85(m, 6H); 4.0–4.2(m, 1H); 4.8–4.95(overlapping d, 0.5H); 5.05–5.2(m,2.5H); 7.4(s,5H).

Mass spectrum M+, 441.

The aforementioned intermediate (0.24 gm) was then stirred 12 hours in a solution of 30% HBr in acetic acid (5 ml . The reaction mixture was evaporated in vacuo, dissolved in 5 ml of H$_2$O, and washed twice with diethyl ether. The aqueous layer was evaporated in vacuo, dissolved in 5 ml of concentrated HCL and stirred 3 days at 50° C. and was evaporated in vacuo. The hydrochloride salt was dissolved in 1 ml of methanol and diluted with 20 ml of propylene oxide. A solid Precipitated which was filtered and washed with ether to give 0.075 gm of the title compound as a hygroscopic glass.

Product spectra:

NMR (D$_2$O) 0.55–0.9(m,9H); 0.95–1.2(m, 3H); 1.3–1.65(m( 6H); 1.7–1.9(m, 1H); 2.0–2.15(m, 1H); 2.45–2.65(br s, 1H); 3.2–3.35(br s, 1H).

Mass spectrum (FAB) M+1, 280.

EXAMPLE 9

1-Aminopropyl-[2-carboxy-4-phenyl-1-butyl]phosphinic Acid

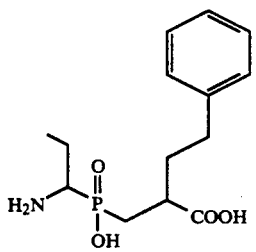

The title compound was analogously prepared according to procedure in Example 8, using methylphenylethyl acrylate.

Product spectra:

NMR (CD3OD) 1.0–1.3 t, 3H); 1.7–2.4(m, 5H); 2.5–2.9(m, 4H); 3.3–3/6(m, 1H); 7.2(s, 5H).

Mass spectrum M+H, 300.

EXAMPLE 10

1-Aminopropyl-2-carboxy-1-butyl]phosphinic acid

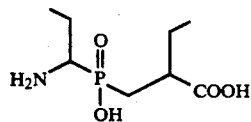

The title compound was analogously prepared according to procedure in Example 8, using (methyl ethylacrylate). Product: TLC (silica, 1:1:1:1, n-butanol: water: ethyl acetate: acetic acid) $R_f$=0.5.

Product spectra:

NMR (D2O) 0.8–1.2 (overlapping t,6H); 1.4–2.5(m, 6H); 2.7–3.1(m, 1H); 3.8–4.2(m, 1H).

Mass spectrum M-H, 222.

EXAMPLE 11

1-Aminopropyl-[2-carboxy-1-hexyl]phosphinic acid

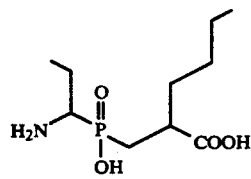

The title compound was analogously prepared according to the Procedure in Example 8, using (methyl-n-butyl acrylate) in 17% overall yield.

Product spectra:

TLC (silica, 1:1:1:1, n-butanol:water:ethyl acetate: acetic acid) $R_f$=0.61.

NMR (D2O) 0.6–0.8 (t, 3H); 0.95–1.1(t, 3H); 1.1–1.3(m, 4H); 1.45–2.05(m, 6H); 2.6–2.8(m, 1H); 3.1–3.3(m, 1H).

Mass spectrum M-H, 250.

EXAMPLE 12

1-Amino-2-phenylethyl-[2-carboxy-1-hexyl]-phosphinic acid

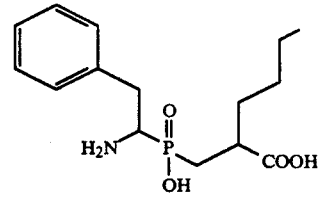

The title compound was analogously prepared according to procedures in Examples 2, 4 and 8.

TLC (silica, 1:1:1:1, n-butanol: water: ethyl acetate:acetic acid) $R_f$=0.73.

NMR (D2O) 0.65–0.75 (t, 3H); 1.2–1.4(m, 4H); 1.4–1.7(m, 2H); 1.8–2.0(m, 1H); 2.05–2.2(m, 1H); 2.5–2.65(m, 1H); 2.7–3.1(m, 2H); 3.7–3.8(m, 1H).

Mass spectrum M-H, 312.

EXAMPLE 13

(1-Amino-2-cyclohexylethyl)-2-carboxy-5-(4-pyridyl)-pentyl phosphinic acid

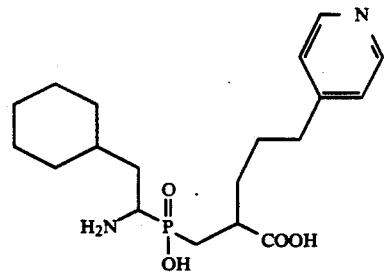

The title compound was obtained by analogous methods described in Examples 5 and 8.

Product spectra:

NMR (300 MHz, D2O); 8.58 (d,2H,6 Hz); 2.92 (br s,2H); 7.88 (d,2H,6 Hz); 2.61 (br s,1H); 4.25 (m,1H); 2.1 (m,1H); 3.20 (m,1H); 0.8–1.8(m,17H)

Mass spectrum (FAB): 383 (M+H,100%)

EXAMPLE 14

1-Amino-2-cyclohexylethyl-[2-carboxy-(4-methyl)-1-pentyl phosphinic acid

The compound was analogously prepared according to the procedures outlined in Examples 6 and 8.

EXAMPLE 15A

Methyl (1-(BOC)amino-2-cyclohexylethyl)-(2-carbomethoxy-4-methyl-2-(E & Z -butenyl)phosphinate

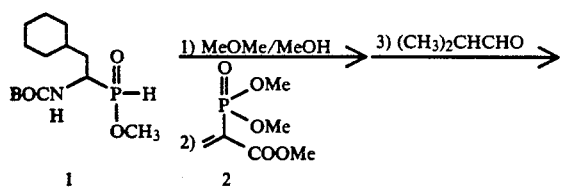

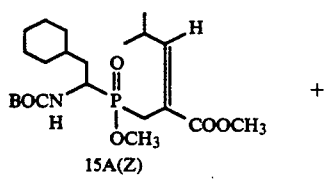

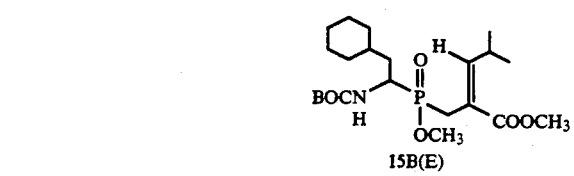

A solution of 0.504 g (1.64 mmol) methyl-N-BOC-1-amino-2-cyclohexylethyl phosphinate (Example 4) in 2.5 mL dry methanol at 0° C. was treated dropwise over ten minutes with 0.90 mL of 2.0N methanolic sodium methoxide (1.8 mmol, 1.1 eq). When addition of the base is complete, 0.38 mL (0.48 g, 2.44 mmol, 1.5 eq.) of 2-trimethylphosphono-acrylate (Fluka) was added dropwise over 2 minutes. The mixture is warmed to room temperature and stirred for 30 minutes. At this time, tlc analysis (ethyl acetate/acetonitrile/methanol 9:1:.5; E. Merck 0.25 mm silica plates) indicates complete disappearance of 1 ($R_f$ 0.8) with formation of a new, more polar material with $R_f$ of 0.3.

The mixture was re-cooled to 0° and 0.30 mL (0.24 g, 3.3 mmol, 2.0 eq) of distilled isobutyraldehyde (Aldrich) was added dropwise over 2 minutes. The mixture was warmed to room temperature when the addition of the aldehyde was complete. After 1 hour at room temperature, tlc analysis (as above) indicates complete disappearance of the polar intermediate and formation of a new, UV active material at higher rf.

The mixture was diluted with ethyl acetate to a total volume of 30 mL and washed with pH 7.0 phosphate buffer (2×10 mL). The organic layer was separated and washed once with 5 ml of saturated aqueous sodium chloride and dried over magnesium sulfate. After filtration and removal of volatiles in vacuo, the crude product was purified by medium pressure liquid chromatography, eluting with 9:1 EtOAc:CH$_3$CN. Two major products were isolated; fraction A (0.190 g, 0.43 mmol, 26%) and fraction B (0.217 g, 0.49 mmol, 30%). Fraction A, which is eluted form the column first, is identified as the 15A Z isomer by analysis of its 300 MHz proton NMR spectrum (olefinic proton resonance at 6.68ppm (CDCl$_3$). Fraction B is the E isomer 15B (olefinic proton resonance at 6.03 ppm).

Product spectra:

| NMR (300 MHz, CDCl$_3$) | | | |
|---|---|---|---|
| Z isomer | | E isomer | |
| 6.68(m, 1H) | 3.70(d, 1.5H, 11Hz) | 6.03(m, 1H) | 3.72(d, 3H, 11Hz) |
| 5.09(d, .5H, 11Hz) | 2.8–3.1(m, 2H) | 4.82(d, .5H, 11Hz) | 3.25(m, 1H) |
| 4.64(d, .5H, 11Hz) | 2.77(m, 1H) | 4.56(d, .5H, 11Hz) | 2.7–3.1(m, 2H) |
| 4.12(m, 1H) | 1.88(s, 9H) | 4.12(m, 1H) | 1.89(m, 1H) |
| 3.80(s, 1.5H) | 1.48(s, 9H) | 3.80(s, 1.5H) | 1.47(s, 9H) |
| 3.78(s, 1.5H) | 0.7–1.8(m, 18H) | 3.79(s, 1.5H) | 0.7–1.8(m, 18H) |
| 3.73(d, 1.5H, 11Hz) | | | |

| Analysis: | calc. for C$_{22}$H$_{40}$NO$_6$P | found (Z) | found (E) |
|---|---|---|---|
| C: | 59.31 | 59.07 | 59.47 |
| H: | 9.05 | 8.86 | 8.82 |
| N: | 3.14 | 3.08 | 3.15 |

Mass spectra (FAB): 15A: 446 (M+H,36%), 390 (M+H-tBu,65%). 15B: 446 (M+H,48%), 390 (M+H-tBu,100%).

EXAMPLE 15B (1-Amino-2-cyclohexylethyl) 2-carboxy-4-methyl-(E & Z)-2-butenyl phosphinic acids (15C & 15D)

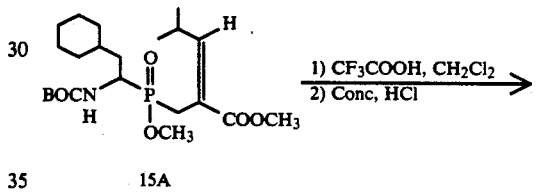

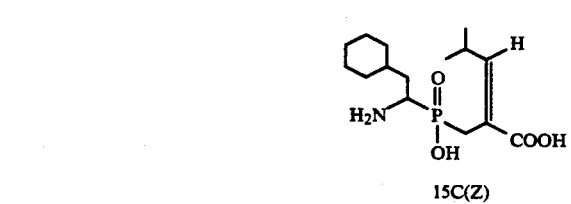

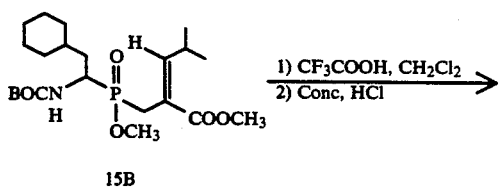

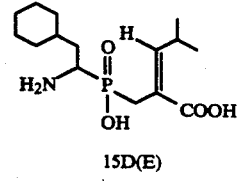

A solution of 157 mg (0.353 mmole) BOC-ester 15A in 3 mL distilled methylene chloride at room temperature was treated with 1 mL anhydrous trifluoroacetic acid. After 30 minutes at room temperature, the reaction mixture was concentrated and all remaining volatiles removed under vacuum. The oily residue was taken up in 5 mL of concentrated hydrochloric acid and heated at 50° C. for 18 hours.

The reaction mixture was concentrated under vacuum to a colorless oil which was redissolved in 5 mL distilled water and lyophilized. Compound 15C was thus obtained as a colorless solid (97 mg, 0.27 mmole, 77%); homogeneous by tlc.

Similarly, the E isomer 15D was analogously obtained in 82% yield from BOC-ester 15B by the route described above.

Product spectra:

| NMR (300MHz, D$_2$O): Z isomer 15C: | |
|---|---|
| 6.82(dd, 1H) | 2.7(m, 1H) |
| 3.38(m, 1H) | 1.5–1.8(m, 8H) |
| 2.90(d, 2H) | 0.9–1.5(m, 11H) |

Mass Spectrum (FAB): 318 (M+H,33%)

| Analysis: | |
|---|---|
| calc. for C$_{18}$H$_{32}$NO$_4$PHCl | found |
| C; 54.89 | 54.21 |
| H; 8.44 | 7.67 |
| N; 3.56 | 3.44 |

Analytical TLC (EtOAc/n-BuOH/HOAc/H$_2$O, 1:1:1:1): R$_f$=0.78.

EXAMPLE 15C (1(R)-Amino-2-cyclohexylethyl)2-carboxyl-4-methyl-2-(Z)-butenyl phosphinic acid (15E)

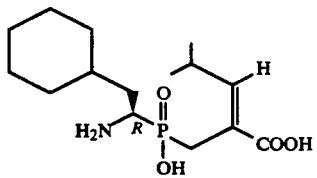

15E

The title compound was synthesized from methyl N-BOC-1(R)-amino-2-cyclohexylethylphosphinate (Example 4A) according to the procedures described in Examples 15A and 15B.

NMR (300 MHz,D$_2$O): 6.82 (dd, 1H); 2.7 (m, 1H); 3.38 (m, 1H); 1.5–1.8 (m, 8H); 2.90 (d, 2H); 0.9–1.5 (m, 11H)

Mass Spectrum (FAB): 318 (M+H, 38%)

Analytical TLC (EtOAc/n-BuOH/HOAc/H$_2$O; 1:1:1:1): R$_f$=0.80

EXAMPLE 16

Methyl (1-t-butoxycarbonylamino-2-cyclohexylethyl) 2-carbomethoxy-3-cyclohexyl-2(E & Z)-propenyl phosphinate

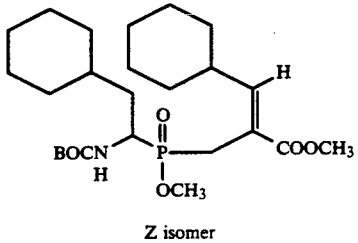

Z isomer

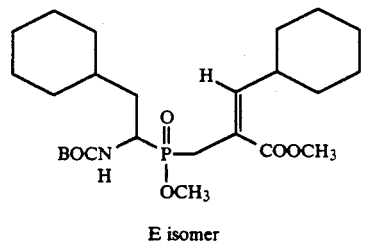

E isomer

The title compounds were analogously synthesized in 23% and 24% yields from methyl-N-BOC-1-amino-2-cyclohexylethyl phosphinate (Example 4), 2-trimethylphosphonoacrylate and cyclohexanecarboxaldehyde (Aldrich) by the procedure described in Example 15A. Both compounds are obtained as mixtures of two diastereomers at phosphorus. Product spectra:

| NMR (300 MHz, CDCl$_3$) | | | |
|---|---|---|---|
| Z isomer | | E isomer | |
| 6.79(m, 1H) | 3.68(d, 1.5H, 16Hz) | 7.35(m, 5H) | 3.75(s, 3H) |
| 5.52(d, .5H, 10Hz) | 2.95(m, 2H) | 5.97(m, 1H) | 3.69(m, 1.5H, 15Hz) |
| 4.96(d, .5H, 10Hz) | 2.43(m, 1H) | 5.22(d, .5H, 10Hz) | 3.64(m, 1.5H, 15Hz) |
| 4.19(m, 1H) | 1.87(m, 1H) | 5.14(s, 2H) | 2.7–3.0(m, 3H) |
| 3.75(s, 1.5H) | 1.45(s, 9H) | 4.90(d, .5H, 10Hz) | 1.85(m, 1H) |
| 3.73(s, 1.5H) 3.72(d, 1.5H, 16Hz) | 0.8–1.8(m, 22H) | 4.16(m, 1H) | 0.7–1.8(m, 22H) |

| Analysis: | | |
|---|---|---|
| calc. for C$_{25}$H$_{44}$NO$_6$P | Z isomer | E isomer |
| C; 61.84 | 61.14 | 61.44 |
| H; 9.13 | 8.71 | 8.93 |
| N; 2.88 | 2.86 | 2.94 |

Mass spectrum (FAB): Z isomer: 486 (M+H,34%). E isomer: 486 (M+H,5%).

EXAMPLE 17

(1-Amino-2-cyclohexylethyl) 2-carboxy-3(Z)-cyclohexyl-2-propenyl phosphinic acid

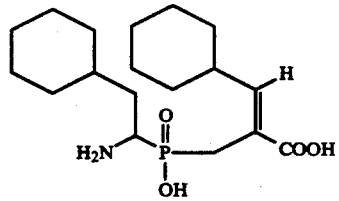

The Z isomer of Example 16 was dissolved in 1 mL glacial acetic acid, treated with 10 mL concentrated hydrochloric acid then heated at 100° for 90 minutes. The mixture was cooled, diluted with 20 mL distilled water and washed with ether (3×10 mL). The aqueous layer was filtered and solvents removed under vacuum to afford the title compound in 88% yield as a white powder.

Product spectra:
NMR (300 MHz, CD$_3$OD): 6.B3 (dd,1H): 2.4B m,1H); 3.39 (m,1H): 0.8–1.9 (m,23H); 2.95 (m,2H)
Mass spectrum (FAB); 358 (M+H,100%)

Analytical TLC (EtOAc/n-BuOH/HOAc/H₂O; 1:1:1:1); R_f=0.79.

| Analysis: | |
|---|---|
| calc. for C₁₈H₃₂NO₄P.HCl | found |
| C: 54.89 | 54.21 |
| H: 8.44 | 7.67 |
| N: 3.56 | 3.44 |

EXAMPLE 17A (1(R)-Amino-2-cyclohexylethyl)2-carboxyl-3(Z)-cyclohexyl-2-propenyl phosphinic acid (15E)

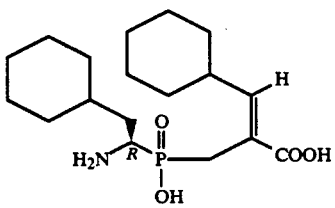

The title compound was synthesized from methyl N-BOC-1(R)-amino-2-cyclohexylethylphosphinate (Example 4A) according to the procedures described in Examples 15A and 15B.

NMR 300 MHz, CD₃OD): 6.83 (dd, 1H); 2.48 (m, 1H); 3.39 (m, 1H); 0.8-1.9 (m, 23H); 2.95 (m, 2H)
Mass Spectrum (FAB): 358 (M+H, 100%)
Analytical TLC (EtOAc/n-BuOH/HOAc/H₂O; 1:1:1:1): R_f=0.75

EXAMPLE 18

Methyl (1-t-butoxycarbonylamino-2-cyclohexylethyl) 2-carbomethoxy-3-cyclohexyl-1-propyl phosphinate

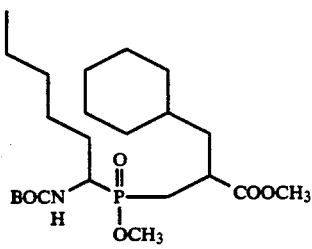

The Z and E isomers described in Example 16 were combined in methanol and hydrogenated over 10% palladium on carbon (20% catalyst by weight) at 40 psi overnight. The crude product was purified by medium pressure liquid chromatography, eluting with 9:1 EtOAc/CH₃CN. The title compound was obtained as two fractions; fraction 1 eluted first and contained three diastereomers while fraction 2 contained a single diastereomer, as determined by 300 MHz NMR.

Product spectra:

| NMR (300 MHz, CDCl₃): | | | |
|---|---|---|---|
| Fraction 1 | | Fraction 2 | |
| 4.5-4.7(m, 1H) | 2.15(m, 1H) | 4.70(d, 1H, 11Hz) | 2.93(m, 1H) |
| 4.05(m, 1H) | 1.45(s, 9H) | 4.13(m, 1H) | 2.16(m, 1H) |
| 3.70(m, 6H) | 0.8-1.9(m, 27H) | 3.70(s, 3H) | 1.45(s, 9H) |

| NMR (300 MHz, CDCl₃): | | |
|---|---|---|
| Fraction 1 | Fraction 2 | |
| 2.90(m, 1H) | 3.68(d, 3H, 10Hz) | 0.8-1.9(m, 27H) |

Mass Spec (FAB): F1: 488 (M+H,30%). F2: 488 (M+H,40%).

EXAMPLE 19

(1-Amino-2-cyclohexylethyl)-2-carboxy-3-cyclohexyl-1-propyl phosphinic acid

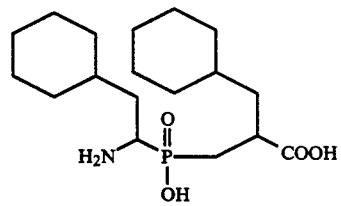

Fractions F1 and F2 (Example 18) were combined and treated with 30% HBr in acetic acid for hours at room temperature. The mixture was diluted with water, washed with ether, filtered and all volatiles removed under vacuum. The title compound was isolated as its hydrobromide salt.

Product spectra:
NMR 300 MHz, CD₃OD): 3.4 (m,1H); 2.3 (m,1H); 2.9 (m,1H); 0.9-2.0 (m,25H)
Mass spectrum (NIFAB): 358 (M-H,100%)

EXAMPLE 20

Methyl (1-t-butoxycarbonylamino-1-hexyl) 2-carbomethoxy-2(E & Z)-octenyl phosphinate

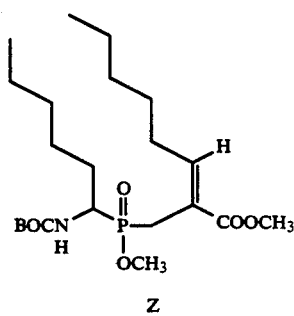

Z

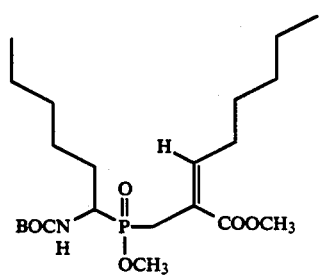

E

The title compounds were analogously synthesized in 31% yield from methyl-1-BOC-amino-n-hexylphosphinate (Example 4A) by the method described in Example 15.

Product Spectra:

| NMR (300 MHz, CDCl₃): Z isomer; | |
|---|---|
| 7.00(m, 1H) | 3.71(d, 1, 5H, 12Hz) |
| 5.13(d, .5H, 11Hz) | 2.95(m, 2H) |
| 4.68(d, .5H, 11Hz) | 2.31(m, 2H) |
| 3.96(m, 1H) | 1.2-2.0(m, 14H) |
| 3.80(s, 1.5H) | 1.48(s, 9H) |
| 3.79(s, 1.5H) | .90(m, 6H) |
| 3.74(d, 1.5H, 12Hz) | |

Mass spectrum (FAB): Z isomer) 448 (M+H,52%)

| Analysis: (Z isomer) | |
|---|---|
| calc. for C₂₂H₄₂NO₆P | found |
| C; 59.04 | 58.01 |
| H; 9.45 | 9.02 |
| N; 3.13 | 2.92 |

EXAMPLE 21

(1-Aminohexyl) 2-carboxy-2(Z)-octenyl phosphinic acid

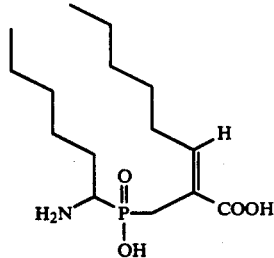

The title compound was analogously obtained by deprotection of the Z isomer described in Example 20 by the route described in Example 15B.

Product Spectra:
NMR (300 MHz, CD₃OD): 7.05 (m,1H); 1.3-2.1 (m,14H); 2.95 (m,3H); 0.95 (m,6H); 2.36 (m,2H)
Mass spectrum (NIFAB): 318 (M-H,100%)

EXAMPLE 22

Methyl (1-t-butoxycarbonylamino-1-hexyl)-2-carbomethoxy-1-octyl phosphinate

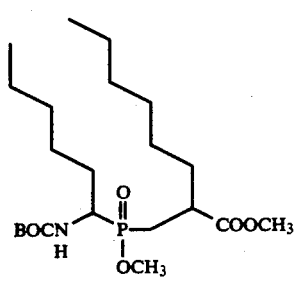

The intermediates described in Example 20 were combined and hydrogenated according to the procedure described in Example 18. The title compound was obtained as two fractions; fraction 1 (64%) contained three diastereomers while fraction 2 (24%) contained a single diastereomer.

Product Spectra:

| NMR (300 MHz, CDCl₃) | | | |
|---|---|---|---|
| fraction 1; | | fraction 2; | |
| 4.55-4.70 (m, 1H) | 1.80(m,.2H) | 4.75(d, 1H, 11Hz) | 2.23(m, 1H) |
| 3.90(m, 1H) | 1.43(s, 9H) | 3.95(m, 1H) | 1.44(s, 9H) |
| 3.70(m, 6H) | 1.1-1.7(m, 17H) | 3.70(s, 3H) | 1.2-1.9(m, 19H) |
| 2.68(m, 1H) | 0.85(m, 6H) | 3.68(d, 3H, 10Hz) | 0.9.(m, 6H) |
| 2.20(m, 1H) | | 2.70(m, 1H) | |

Mass Spec (FAB): fraction 1; 450 (M+H,14%). fraction 2; 450 (M+H,18%).

| Analysis (fraction 1) | |
|---|---|
| calc. for C₂₂H₄₄NO₆P | found |
| C: 58.78 | 58.78 |
| H: 9.87 | 9.51 |
| N: 3.12 | 3.39 |

EXAMPLE 23

(1-Amino-1-hexyl) 2-carboxy-1-octyl phosphinic acid

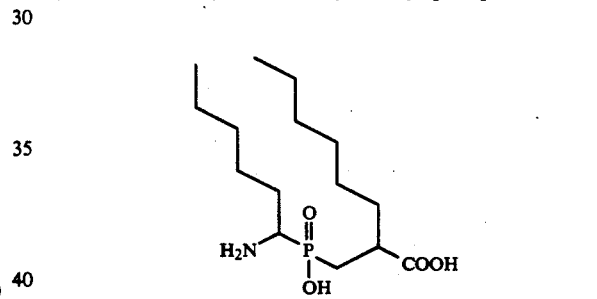

The two fractions described in Example 22 were combined and deprotected following the procedure described in Example 19. The title compound was obtained as its hydrobromide salt.

Product spectra:
NMR (300 MHz, CD₃OD): 2.85 (m,1H); 1.2-2.1 (m,19H); 2.32 (m,1H); 0.9 (m,6H)
Mass spectrum (NIFAB): 320 (M-H,100%)

EXAMPLE 24

Methyl (1-t-butoxycarbonylamino-1-hexyl) 2-carbomethoxy-4-cyclopentyl-2(E & Z)-butenyl phosphinate

Z

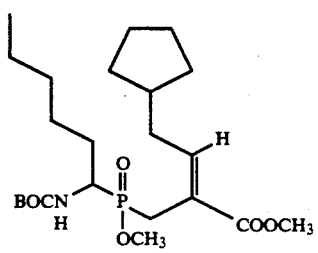

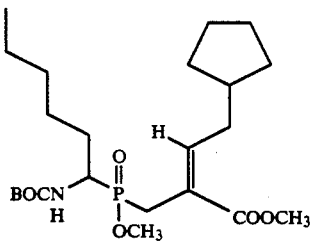

The title compounds were analogously prepared in 29% yield from methyl-1-BOC-amino-n-hexylphosphinate (Example 4A) according to the procedure described in Example 15A.

Product spectra:
Mass spectrum: (FAB) 460 (M+H,43%) Z isomer

| Analysis: | |
|---|---|
| calc. for $C_{23}H_{42}NO_6P$ | found |
| C: 60.11 | 58.27 |
| H: 9.21 | 8.91 |
| N: 3.05 | 3.22 |

EXAMPLE 25

(1-Aminohexyl) 2-carboxy-4-cyclopentyl-2(Z)-butenyl phosphinic acid

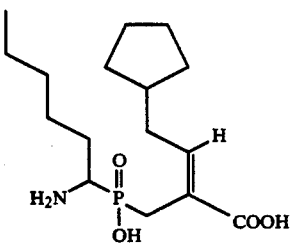

From the intermediate described in Example 24, the title compound was analogously obtained in 82% yield according to the procedure described in Example 15B.

Product spectra: NMR (300 MHz, CD$_3$OD): 7.10 (m,1H); 2.00 (m,2H); 3.35 (m,1H); 1.1–1.9 (m, H); 3.00 (m,2H); 0.95 (t,3H); 2.35 (m,2H)

EXAMPLE 26

Methyl (1-t-butoxycarbonylamino-1-hexyl) 2-carbomethoxy-4-cyclopentyl-1-butyl phosphinate

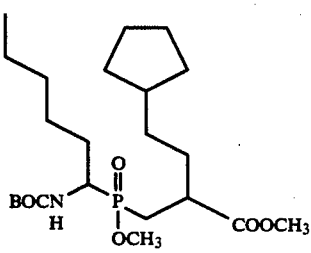

The intermediates described in Example 24 were combined and hydrogenated according to the procedure described in Example 18. The title compound was obtained as two fractions; fraction 1 contained three diastereomers while fraction 2 contained a single diastereomer.

Product spectra:
Mass spectrum (FAB): fraction 1; 462 (M+H,50%). fraction 2; 462 (M+H,50%).

| | Analysis: | |
|---|---|---|
| | found | |
| calc. for $C_{23}H_{44}NO_6P$ | fraction 1 | fraction 2 |
| C: 59.85 | 59.65 | 57.90 |
| H: 9.61 | 9.15 | 9.35 |
| N: 3.03 | 3.27 | 2.23 |

EXAMPLE 27

(1-Amino-1-hexyl) 2-carboxy-4-cyclopentyl-1-butyl phosphinic acid

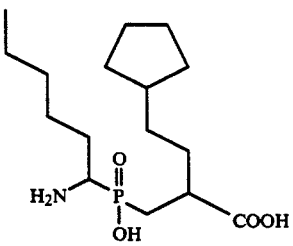

The fractions described above were combined and deprotected according to the procedure described in Example 19. The title compound was obtained as the hydrobromide salt.

Product spectra:
NMR (300 MHz, CD$_3$OD): 3.40 (m,1H); 1.0–2.0 (m,21H); 2.85 (m,1H); 0.95 (t,3H,6 Hz); 2.30 (m,1H)
Mass Spec (FAB): 332 (M-H,100%)

EXAMPLE 28

Methyl (1-t-butoxycarbonylamino-2-cyclohexylethyl) 2-carbomethoxy-2(E and Z)-octenyl phosphinate

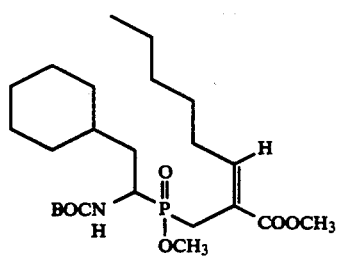

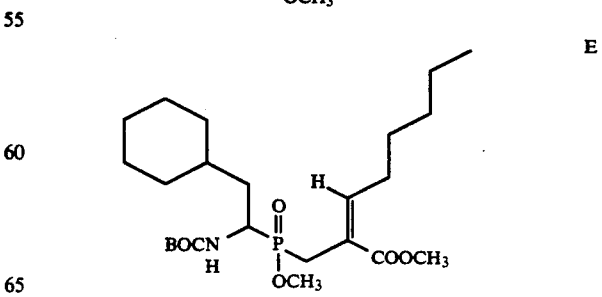

The title compounds were analogously synthesized in 42% yield from methyl N-BOC-1-amino-2-cyclohexylethyl phosphinate (Example 4) by the method described in Example 15A.

Product spectra:
Mass Spec (FAB): 474 (M+H,21%)

| Analysis | |
|---|---|
| calc. for C24H44NO6P | found |
| C; 60.87 | 60.42 |
| H; 9.37 | 8.86 |
| N; 2.96 | 2.99 |

Analytical TLC (EtOAc/CH3CN/CH3OH; 9:1:.5) R$_f$=0.71

EXAMPLE 29

(1-Amino-2-cyclohexylethyl) 2-carboxy-2(Z)-octenyl phosphinic acid

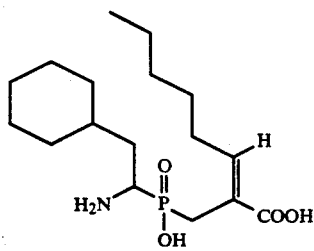

Deprotection of the Z isomer of Example 28 by the methods described in Example 15B afforded the title compound in 61% yield.

Product spectra:
NMR (300 MHz, CD3OD): 7.08 (m,1H); 2.33 (m,2H); 3.43 (m,1H); 0.8-1.8 (m,22H); 3.00 (m,2H)
Mass spectrum (FAB): 346 (M+H,21%)

| Analysis | |
|---|---|
| calc. for C17H32NO4P.HCl | found |
| C: 53.47 | 54.38 |
| H: 8.71 | 8.86 |
| N: 3.67 | 3.46 |

EXAMPLE 30

Methyl (1-t-butoxycarbonylamino-2-cyclohexylethyl) 2-carbomethoxy-1-octyl phosphinate

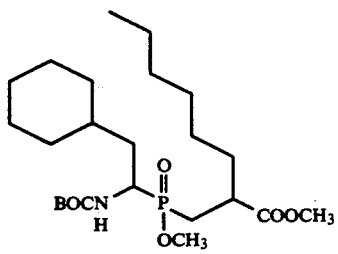

The intermediates described in Example 28 (as a mixture of E and Z isomers) were hydrogenated as described in Example 18 to afford the title compound which was obtained as two fractions. Fraction 1 contained three diastereomers while fraction 2 contained a single diastereomer.

Product spectra:

Mass spectrum (FAB): fraction 1; 476 (M+H,63%). fraction 2; 476 (M+H,46%).

| Analysis: fraction 1 | |
|---|---|
| calc. for C24H46NO6P | found |
| C: 60.61 | 60.26 |
| H: 9.75 | 9.18 |
| N: 2.95 | 2.82 |

EXAMPLE 31

(1-Amino-2-cyclohexylethyl) 2-carboxy-1-octyl phosphinic acid

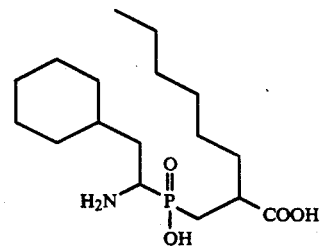

The two fractions obtained in Example 30 were combined and deprotected as described in Example 19 to afford the title compound as its hydrobromide salt.

Product spectra: Mass spectrum (FAB): 348 (M+H,10%)

EXAMPLE 32

Methyl (1-t-butoxycarbonylamino-2-cyclohexylethyl) 2-carbomethoxy-4-cyclopentyl-2(E & Z)-butenyl phosphinate

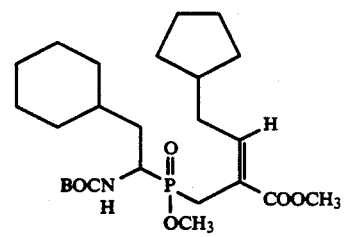

Z

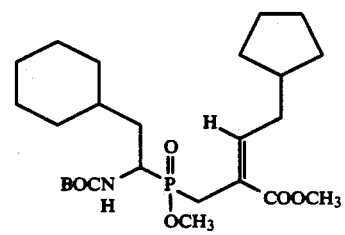

E

The title compound was analogously prepared in 44% yield from methyl N-BOC-1-amino-2-cyclohexylethyl phosphinate (Example 4) by the method described in Example 15A.

Product spectra:
Mass spectrum (FAB): 486 (M+H,57%) Z isomer

| Analysis: | |
|---|---|
| calc. for $C_{25}H_{44}NO_6P$ | found |
| C: 61.84 | 61.57 |
| H: 9.13 | 8.31 |
| N: 2.88 | 3.16 |

EXAMPLE 33

(1-Amino-2-cyclohexylethyl) 2-carboxy-4-cyclopentyl-2 (Z)-butenyl phosphinic acid

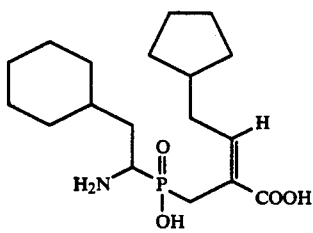

Deprotection of the Z isomer of Example 32 by the method described in Example 15B afforded the title compound in 44% yield.

Product spectra:
NMR (300 MHz, CD$_3$OD): 7.09 (m,1H); 2.39 (m,2H); 3.25 (m,1H); 2.02 (m,1H); 2.95 (M,2H); 0.8–1.9 (m,21H)
Mass spectrum (FAB): 357 (M+,100%)

| Analysis: | |
|---|---|
| calc. for $C_{18}H_{32}NO_4P\cdot HCl\cdot.5H_2O$ | found |
| C: 53.66 | 53.62 |
| H: 8.51 | 8.47 |
| N: 3.47 | 3.40 |

Analytical TLC: (EtOAc/n-BuOH/HOAc/H2O; 1:1:1:1) R$_f$=0.86

EXAMPLE 33A (1(R)-Amino-2-cyclohexylethyl)2-carboxy-4-cyclopentyl-2(Z)-butenyl phosphinic acid

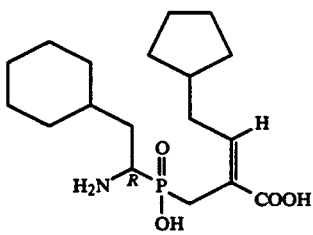

The title compound was synthesized from methyl N-BOC-1(R)-amino-2-cyclohexylethylphosphinate (Example 4A) according to the procedures described in Examples 15A and 15B.

NMR (300 MHz, CD$_3$OD): 7.09 (m,1H); 2.39 (m,2H); 3.25 (m,1H); 2.02 (m,1H); 2.95 (m,2H); 0.8–1.9 (m,23H)
Mass spectrum (FAB): 357 (M+, 100%)
Analytical TLC (EtOAc/n-BuOH/HOAc/H2O; 1:1:1:1): R$_f$=0.86

EXAMPLE 34

Methyl (1-t-butoxycarbonylamino-2-cyclohexylethyl) 2-carbomethoxy-4-cyclopentyl-1-butyl phosphinate

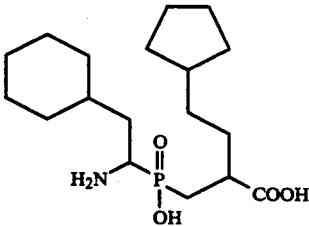

The Z & E isomer of Example 32 were combined and hydrogenated by the method described in Example 18 to afford the title compound as two fractions; fraction 1 contained three diastereomers and fraction 2 contained a single diastereomer.

Product spectra:

| NMR (300 MHz, CDCl$_3$): | | | |
|---|---|---|---|
| fraction 1: | | fraction 2: | |
| 4.60(m, 1H) | 2.22(m, 1H) | 4.73(d, 1H, 11Hz) | 2.84(m, 1H) |
| 4.05(m, 1H) | 1.87(m, 2H) | 4.15(m, 1H) | 2.25(m, 1H) |
| 3.72(m, 6H) | 1.47(s, 9H) | 3.73(s, 3H) | 1.48(s, 9H) |
| 2.80(m, 1H) | 0.8–1.8(m, 25H) | 3.68(d, 3H, 10Hz) | 0.8–2.0(m, 25H) |

Mass spectrum (FAB): fraction 1: 488 (M+H,35%). fraction 2: 488 (M+H,43%).

| | Analysis: | |
|---|---|---|
| | | found |
| calc. for $C_{25}H_{46}NO_6P$ | fraction 1 | fraction 2 |
| C: 61.58 | 61.73 | 60.99 |
| H: 9.51 | 9.05 | 9.22 |
| N: 2.87 | 2.58 | 2.33 |

EXAMPLE 35

(1-Amino-2-cyclohexylethyl) 2-carboxy-4-cyclopentyl-1-butyl phosphinic acid

The two fractions described in Example 34 were combined and deprotected by the method described in Example 19 to afford the title compound as the hydrobromide salt.

Product spectra:
NMR (300 MHz,CD$_3$OD): 3.59 (m,1H); 2.40 (m,1H); 2.84 (m,1H); 0.8–2.0 (m,26H)
Mass spectrum (FAB): 358 (M-H,100%)

EXAMPLE 36

Methyl (1-t-butoxycarbonylamino-1-hexyl) 2-carbomethoxy-3-cyclohexyl-2(E & Z)-propenyl phosphinate

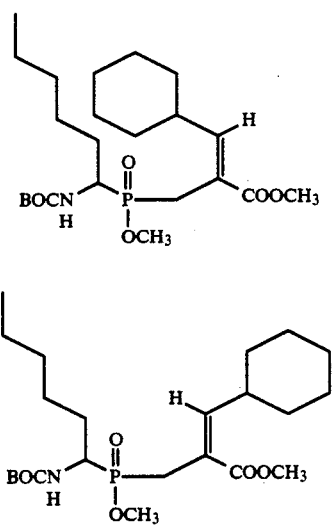

The title compounds were analogously prepared in 20% yield from methyl-1-BOC-amino-n-hexylphosphinate (Example 4A) by the method described in Example 15A.

Product spectra:
Mass spectrum: (FAB) 460 (M+H,48%)

| Analysis: | |
|---|---|
| calc. for C$_{23}$H$_{42}$NO$_6$P | found |
| C: 60.11 | 58.48 |
| H: 9.21 | 8.55 |
| N: 3.05 | 3.19 |

EXAMPLE 37

(1-Aminohexyl) 2-carboxy-3-cyclohexyl-2(Z)-propenyl phosphinic acid

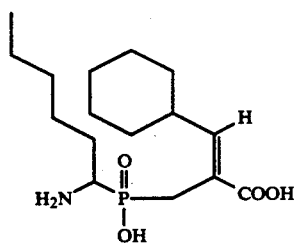

The Z isomer of Example 36 was deprotected in 60% yield according to the procedure described in Example 15B to afford the title compound.

Product spectra:
NMR (300 MHz, CD$_3$OD): 6.82 (m,1H); 2.52 (m,1H); 3.21 (m,1H); 1.1–2.1 (m,18H); 2.91 (m,2H); 0.95 (t,3H)
Mass spectrum: (FAB) 330 (M-H,100%)

| Analysis: | |
|---|---|
| calc. for C$_{16}$H$_{30}$NO$_4$P.HCl | found |
| C: 52.24 | 52.59 |
| H: 8.49 | 8.53 |
| N: 3.81 | 3.69 |

Analytical TLC: (EtOAc/n-BuOH/HOAc/H$_2$O; 1:1:1:1) R$_f$=0.83

EXAMPLE 38

Methyl (1-t-butoxycarbonylamino-1-hexyl) 2-carbomethoxy-3-cyclohexyl-1-propyl phosphinate

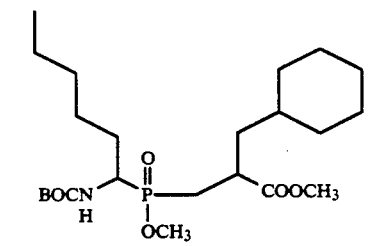

The intermediates described in Example 36 were combined and hydrogenated according to the procedure described in Example 18. The title compound was obtained as two fractions; fraction 1 contains three diastereomers while fraction 2 contains a single diastereomer.

Product spectra:
Mass spectrum (FAB): fraction 1; 462 (M+H,50%). fraction 2; 462 (M+H,33%).

| Analysis: | | |
|---|---|---|
| | found | |
| calc. for C$_{23}$H$_{44}$NO$_6$P | fraction 1 | fraction 2 |
| C: 59.85 | 59.80 | 57.77 |
| H: 9.61 | 9.32 | 8.96 |
| N: 3.03 | 3.21 | 2.31 |

EXAMPLE 39

(1-Amino-1-hexyl) 2-carboxy-3-cyclohexyl-1-propyl phosphinic acid

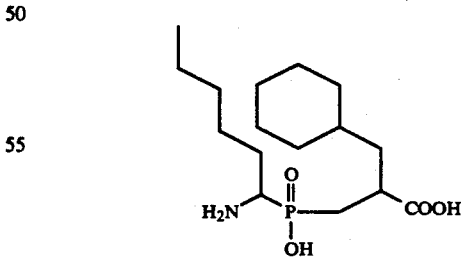

The two fractions described in Example 38 were combined and deprotected following the procedure described in Example 19. The title compound was isolated as its hydrobromide salt.

Product spectra:
NMR (300 MHz,CD$_3$OD): 3.16 (m,1H); 1.2–2.1 (m,21H); 2.93 (m,1H); 1.00 (t,3H,6 Hz); 2.15 (m,1H)
Mass spectrum (FAB): 332 (M-H,100%)

What is claimed is:

1. A DHP inhibiting compound of Formula II:

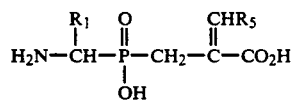

$$H_2N-CH(R_1)-P(=O)(OH)-CH_2-C(CHR_5)-CO_2H \quad \text{II}$$

wherein
$R_1$ is
(a) $C_2-C_{12}$ linear or branched unsubstituted alkyl;
(b) $C_2-C_{12}$ linear or branched substituted alkyl;
(c) $C_2-C_{12}$ linear or branched monoalkenyl;
(d) $C_2-C_{12}$ linear or branched alkynyl;
(e) $C_7-C_{20}$ aralkyl, wherein the alkyl chain is linear or branched $C_1-C_8$ where N is 1 or 2 and the aryl moiety is $C_6-C_{12}$;
(f) $C_3-C_7$ cycloalkyl;
(g) $C_4-C_{10}$ cycloalkylalkyl;

wherein said above values for $R_1$, excluding (a), can be substituted by one or more: $C_1-C_4$ alkoxy, $C_3-C_6$ cycloalkyloxy, $C_3-C_6$ cycloalkylthio, $C_6-C_{12}$ aryloxy, $C_1-C_4$ alkylthio, $C_6-C_{12}$ arylthio, $C_7-C_{10}$ aralkyloxy, $C_7-C_{16}$ aralkylthio;

$R_5$ is
(a) H or $C_1-C_{12}$ linear or branched alkyl;
(b) $C_2-C_{12}$ linear or branched monoalkenyl;
(c) $C_7-C_{20}$ aralkyl, wherein the alkyl chain is linear or branched $C_1-C_8$ and the aryl moiety is $C_6-C_{12}$;
(d) heterocyclic alkyl, wherein the alkyl chain is linear or branched $C_1-C_8$ and the heterocyclic ring is 5-6 membered, aromatic, and containing 1-2 heteroatoms selected from the group consisting of O, N and S;
(e) heterocyclic alkyl, wherein the alkyl chain is linear or branched $C_1-C_8$ and the heterocyclic ring is 5-6 membered, aromatic, containing 1-2 heteroatoms selected from the group consisting of O, N and S, and the heterocyclic ring is fused with a benzene ring;

wherein said above values for $R_5$ can be substituted by one or more: halo, hydroxy, carboxy, $C_1-C_4$ alkoxycarbonyl, $C_7-C_{16}$ arylalkoxycarbonyl, $C_3-C_7$ cycloalkyl, $C_1-C_4$ alkoxy, $C_3-C_6$ cycloalkyloxy, $C_3-C_6$ cycloalkylthio, $C_6-C_{12}$ aryloxy, amino, mono or di-$C_1-C_8$ alkylamino, thio $C_1-C_4$ alkylthio, $C_6-C_{12}$ arylthio, $C_7-C_{16}$ aralkylthio, or the radical $-S-(CH_2)_n-CH(NH_2)COOH$.

2. The compound of claim 1 wherein $R_1$ is cyclohexylmethyl, isobutyl, benzyl, or n-pentyl.

3. The compound of claim 1 wherein:
$R_5$ is
(a) $C_1-C_{12}$ linear or branched alkyl;
(b) $C_2-C_{12}$ linear or branched monoalkenyl;
(c) $C_7-C_{20}$ aralkyl, wherein the alkyl chain is linear or branched $C_1-C_8$ and the aryl moiety is $C_6-C_{12}$;
(d) heterocyclic alkyl, wherein the alkyl chain is linear or branched $C_1-C_8$ and the heterocyclic ring is 5-6 membered, aromatic and containing 1-2 heteroatoms selected from the group consisting of O, N and S;
(e) heterocyclic alkyl, wherein the alkyl chain is linear or branched $C_1-C_8$ and the heterocyclic ring is 5-6 membered aromatic containing 1-2 heteroatoms selected from the group consisting of O, N and S, and the heterocyclic ring is fused with a benzene ring;

wherein said above values from $R_5$ can be substituted by one or more: halo, hydroxy, carboxy, $C_1-C_4$ alkoxycarbonyl, $C_7-C_{16}$ aralkylthio, or the radical $-S-(CH_2)_n-CH(NH_2)COOH$.

4. The compound of claim 3 in which the stereochemical configuration of the carbon attached to $R_1$ is (R) or (SR) and $R_5$ is in the "Z" configuration.

5. The compound of claim 1 being:
(1-amino-2-cyclohexylethyl) 2-carboxy-4-methyl-(E & Z)-2-butenyl phosphinic acids;
(1amino-2-cyclohexylethyl) 2-carboxy-3(Z)-cyclohexyl-2-butenyl phosphinic acid;
(1-aminohexyl) 2-carboxy-2(Z)-octenyl phosphinic acid;
(1-aminohexyl) 2-carboxy-4-cyclopentyl-2(Z)-butenyl phosphinic acid;
(1-amino-2-cyclohexylethyl) 2-carboxy-2(Z)-octenyl phosphinic acid;
(1-amino-2-cyclohexylethyl) 2-carboxy-4-cyclopentyl-2(Z)-butenyl phosphinic acid;
(1-aminohexyl) 2-carboxy-3-cyclohexyl-2(Z)-butenyl phosphinic acid;
[1(R)-amino-2-cyclohexylethyl]-2-carboxy-4-methyl-2(Z)-butenylphosphinic acid;
[1(R)-amino-2-cyclohexylethyl]-2-carboxy-3(Z)-cyclohexyl-2-propenyl phosphinic acid;
[1(R)-amino-2-cyclohexylethyl]-2-carboxy-4-cyclopentyl-2(Z)-butenyl phosphinic acid.

* * * * *

UNITED STATES PATENT AND TRADEMARK OFFICE
CERTIFICATE OF CORRECTION

PATENT NO. : 5,145,990

DATED : September 8, 1992

INVENTOR(S) : W. H. Parsons, W. R. Schoen & A. A. Patchett

It is certified that error appears in the above—identified patent and that said Letters Patent is hereby corrected as shown below:

In claim 1, at line 8, column 39, please place a Roman Numeral Two, "II", below the structural formula, which has been omitted from the patent, but has been part of the application.

Signed and Sealed this

Twenty-eighth Day of September, 1993

Attest:

BRUCE LEHMAN

Attesting Officer     Commissioner of Patents and Trademarks